(12) United States Patent
Ahlers et al.

(10) Patent No.: US 7,173,138 B2
(45) Date of Patent: Feb. 6, 2007

(54) LIGANDS FOR PNICOGEN CHELATE COMPLEXES WITH A METAL OF SUBGROUP VIII AND USE OF THE COMPLEXES AS CATALYSTS FOR HYDROFORMYLATION, CARBONYLATION, HYDROCYANATION OR HYDROGENATION

(75) Inventors: Wolfgang Ahlers, Worms (DE); Rocco Paciello, Bad Dürkheim (DE); Dieter Vogt, Eindhoven (DE); Peter Hofmann, Heidelberg (DE)

(73) Assignee: BASF Aktiengesellschaft, Ludwigshafen (DE)

(*) Notice: Subject to any disclaimer, the term of this patent is extended or adjusted under 35 U.S.C. 154(b) by 399 days.

(21) Appl. No.: 10/473,216

(22) PCT Filed: Mar. 28, 2002

(86) PCT No.: PCT/EP02/03543

§ 371 (c)(1),
(2), (4) Date: Sep. 29, 2003

(87) PCT Pub. No.: WO02/083695

PCT Pub. Date: Oct. 24, 2002

(65) Prior Publication Data

US 2004/0110960 A1   Jun. 10, 2004

(30) Foreign Application Priority Data

Mar. 29, 2001 (DE) .............................. 101 15 689
Aug. 24, 2001 (DE) .............................. 101 41 494

(51) Int. Cl.
*C07F 9/572* (2006.01)
*C07C 29/00* (2006.01)
*C07C 29/03* (2006.01)
*B01J 31/02* (2006.01)

(52) U.S. Cl. ............ 548/101; 548/111; 548/402; 548/412; 568/451; 568/454; 568/909; 502/154; 502/155

(58) Field of Classification Search .......... 548/402, 548/412, 101, 111; 568/451, 454, 909; 502/154, 502/155
See application file for complete search history.

(56) References Cited

U.S. PATENT DOCUMENTS 3,816,452 A   6/1974   Mrowea 5,710,344 A    1/1998   Breikss et al.
5,907,045 A    5/1999   Antognazza et al.
6,881,867 B2*  4/2005   Ahlers et al. .............. 568/451
6,977,312 B2* 12/2005   Ahlers et al. .............. 568/17
2003/0022947 A1  1/2003   McAtee et al.
2003/0055253 A1  3/2003   Ahlers et al.
2005/0020857 A1  1/2005   Volland et al. ............ 564/12
2006/0052645 A1  3/2006   Volland et al. ........... 468/451

FOREIGN PATENT DOCUMENTS

| DE | 102 39 134 | 1/2003 |
|---|---|---|
| EP | 754 715 | 1/1997 |
| WO | 95/30680 | 11/1995 |
| WO | 98/42716 | 10/1998 |
| WO | 99/52632 | 10/1999 |
| WO | 99/52915 | 10/1999 |
| WO | WO 03/018192 | 3/2003 |
| WO | WO 03/062251 | 7/2003 |
| WO | WO 03/066642 | 8/2003 |

OTHER PUBLICATIONS

Organometallics 1995, 14, 3081-3089, Leeuwen et al.
Angew.Chem.2000, 112, Nr. 9, Boerner et al.
Organometallics, 1999, 18,4765-4777, van der Veen et al.
J.Am.Chem.Soc.1995,117,7696-7710, Moloy et al.
Organometallics 2000,19, 1427-1433, Smith et al.
Trzeciak et al., Jorl. of Organometallic Chemistry 552(1998) 159-164, Jorl. CHem. Soc., Dalton Trans. 1831 (1997, J. Organomet. Chem. 575,87(1999), Trzeciak et al., C .R. Acad.Sci. Serie IIc 235(1999).
WO/00/56451 =DE 19913 352 = Derwent Abst, DW 2000-619786.
Organometallics 1998, 17, 3000-3005, Shen et al.
Brunner et al., Chem. Ber. 118, S. 3380=3395(1985).
DE 100 23 471 = Derwent 2002-089784.
P 100 46 026.7 = WO 02/22261= Derwent 2002-393928.
Gimbert et al., J.Org.Chem.1999, 64, 3492-3497.
Benincori et al., J.Org. Chem.2000, 65, 8340-8347.
Organometallics 2000, 19, 2504-2515, van Leeuwen et al.
Patent Absts. of Japan, 2002-047294.
Botteghl et al., "*Preparation of linear long chain dialdehydes by hydroformylation of linear α,ω-dienes or ω-vinylaldehyde acetals*" Journal of Molecular Catalysis A: Chemical 175, 17-25 (2001).

* cited by examiner

*Primary Examiner*—Fiona T. Powers
(74) *Attorney, Agent, or Firm*—Novak Druce & Quigg, LLP

(57) ABSTRACT

Pnicogen chelate compounds which have two pnicogen-containing groups joined to one another via a xanthene-like or triptycene-like molecular skeleton and in which at least one pyrrole group is covalently bound via its nitrogen atom to each pnicogen atom form complexes with metals of transition group VIII which are useful as catalysts for the hydroformylation of olefins.

21 Claims, No Drawings

LIGANDS FOR PNICOGEN CHELATE COMPLEXES WITH A METAL OF SUBGROUP VIII AND USE OF THE COMPLEXES AS CATALYSTS FOR HYDROFORMYLATION, CARBONYLATION, HYDROCYANATION OR HYDROGENATION

The present invention relates to novel pnicogen chelate compounds, to catalysts comprising pnicogen chelate complexes with a metal of transition group VIII of the Periodic Table of the Elements which comprise at least one pnicogen chelate compound of the formula I as ligands and to a process for preparing aldehydes and/or alcohols by hydroformylation of $C_3$–$C_{20}$-olefins using these catalysts. The invention further relates to a process for preparing 2-propylheptanol comprising the hydroformylation of butene, an aldol condensation of the resulting hydroformylation products and the catalytic hydrogenation of the condensation products.

Since the discovery of the hydroformylation reaction by Otto Roelen in 1938, hydroformylation has become the classic example of the use of homogeneous catalysis by means of organometallic catalysts on an industrial scale. Thus, millions of metric tons of aldehydes and/or alcohols are produced worldwide by means of homogeneously catalyzed hydroformylation processes. Catalysts used for this purpose are mainly cobalt carbonyl and rhodium carbonyl compounds which may have been modified in respect of their reactivity and selectivity by means of other ligands, e.g. triphenylphosphine ligands. For the preparation of $C_3$–$C_5$-aldehydes from linear olefins having a terminal double bond (α-olefins), the use of modified rhodium carbonyl compounds has now become the method of choice, while hydroformylation catalyzed by cobalt carbonyl is still used for the preparation of longer-chain aldehydes and/or alcohols, although cobalt catalysis has the disadvantage compared to catalysis using ligand-modified rhodium compounds that the reaction has to be carried out at higher pressure.

The reason for this lies in the different catalytic behavior of these catalyst metals: especially in the preparation of relatively long-chain aldehydes, industrially available olefin mixtures in which both terminal and internal olefins are present frequently serve as starting material. The hydroformylation of terminal olefins can, depending on the position at which the CO molecule is added onto the double bond, form linear aldehydes, also known as n-aldehydes, or branched aldehydes, also known as isoaldehydes. In general, the maximum possible proportion of n-aldehydes in the reaction mixture is desired. While the rhodium-triphenylphosphine catalyst system leads to high n-selectivities in the formation of short-chain aldehydes, this system has not been able to become established in the same way for the hydroformylation of relatively long-chain olefines. Reasons for this are firstly the isomerization of terminal double bonds to internal double bonds which is catalyzed by the rhodium catalyst and takes place to an appreciable extent under the conditions of the hydroformylation reaction and secondly the unsatisfactory hydroformylation activity of the rhodium-triphenylphosphine catalyst opposite internal double bonds.

The hydroformylation of relatively long-chain olefins is of great industrial importance for the preparation of plasticizer alcohols (alcohols for preparing ester plasticizers) and surfactant alcohols. Thus, large amounts of plasticizers are used for modifying the thermoplastic properties of a large number of industrially important products, especially plastics but also surface coatings, coating compositions, sealing compositions, etc. An important class of plasticizers comprises the ester plasticizers, which include, inter alia, phthalic esters, adipic esters, trimellitic esters, phosphoric esters, etc. To prepare ester plasticizers having good use properties, there is a need for plasticizer alcohols which have from about 6 to 12 carbon atoms and have only a small degree of branching (known as semilinear alcohols), and appropriate mixtures thereof. They include, in particular, 2-propylheptanol and alcohol mixtures in which it is present.

DE-A-100 03 482 describes an integrated process for preparing $C_9$-alcohols and $C_{10}$-alcohols from $C_4$ hydrocarbon mixtures comprising butene and butane, in which, inter alia, the hydrocarbon mixture is subjected to a hydroformylation and the resulting $C_5$-aldehydes are subjected to an aldol condensation and subsequent catalytic hydrogenation to form $C_{10}$-alcohols.

As mentioned at the outset, the hydroformylation of olefins having more than 2 carbon atoms results in the formation of mixtures of isomeric aldehydes because of the ability of CO to be added onto each of the two carbon atoms of a double bond. In addition, it is also possible for double bond isomerization, i.e. a shift of internal double bonds to a terminal position and vice versa, to occur. Thus, in the preparation of 2-propylheptanol or of alcohol mixtures having a high 2-propylheptanol content by hydroformylation of butene and subsequent aldol condensation, the hydroformylation can easily result in formation of not only n-valeraldehyde but also undesirable product aldehydes, which adversely affects the economics of the overall process.

If industrial mixtures, for example $C_4$ fractions which are available in large quantities both from FCC plants and from steam crackers and consist essentially of a mixture of 1-butene and 2-butene and generally also butane, are used for the hydroformylation, the hydroformylation catalyst used has to make it possible for terminal olefins (1-butene) to be hydroformylated very selectively and/or has to be able to catalyze a shift of internal double bonds to a terminal position. There is generally great industrial interest in the provision of such hydroformylation catalysts.

Owing to the abovementioned problems, this has recently led to intensive research activity with the aim of developing new ligands, new catalyst systems and processes for the hydroformylation of long-chain and/or internal olefins.

WO 95/30680 and van Leeuwen et al., Organometallics 14, 3081 (1995) describe chelating phosphines having a xanthene backbone whose use in the rhodium-catalyzed hydroformylation of terminal olefins leads to high n-selectivities. However, these catalyst systems are unsuitable for the hydroformylation of internal olefins.

Börner et al., Angew. Chem. 112, 1694 (2000) report the hydroformylation of internal, linear olefins with the aid of rhodium catalysts modified with bisphenol monoether monophosphonites. The n-selectivity of 35–48% achieved using this process is low.

Van Leeuwen et al., Organometallics 18, 4765 (1999), reacted internal olefins over rhodium catalysts which had been modified by means of a xanthene chelate phosphine ligand substituted by two phenoxaphosphine groups and achieved a maximum olefin conversion of 67% after 17 hours.

U.S. Pat. No. 3,816,452 relates to the preparation of differently substituted pyrrolyl-monophosphines and their use as flame retardants.

K. G. Moloy et al., J. Am. Chem. Soc. 117, 7696 (1995) describe the preparation, electronic properties and complexation properties of bis(dipyrrolylphosphino)ethane.

The preparation and physicochemical properties of platinum complexes of this ligand are described in the article by Smith et al, organometallics 19, 1427 (2000). A concrete application of these compounds and their metal complexes for catalytic purposes is not mentioned.

Trzeciak et al. use trispyrrolylphosphine-rhodium complexes for the hydrogenation of arenes (J. Organomet. Chem. 552, 159 (1998)) and for rhodium-catalyzed hydroformylation (J. Chem. Soc., Dalton Trans. 1831 (1997)). In the hydroformylation of 1-hexene, an appreciable proportion of by-products formed as a result of the isomerization of 1-hexene to 2-hexene is found. According to the statements by Trzeciak et al. in J. Organomet. Chem. 575, 87 (1999), rhodium complexes containing diphenyl-2-hydroxyphenylphosphine and trispyrrolylphosphine as ligands are virtually inactive in hydroformylation. C. R. Acad. Sci., Série IIc, 235 (1999) relates to the hydroformylation of vinylsilanes by means of trispyrrolylphosphine-modified rhodium catalysts.

WO 00/56451 relates to cyclic oxaphosphorins substituted on the phosphorus atom by, inter alia, pyrrole derivatives and the use of these as ligands in hydroformylation catalysts.

In Organometallics 1998, 17, pp. 3000–3005, J. Shen et al. describe calorimetric studies on chelating diphosphine ligands including, inter alia, hydrazide-bridged diphenylphosphines and alkylene-bridged dipyrrolylphosphines.

In Chem. Ber. 118, pp. 3380–3395 (1985), H. Brunner and H. Weber describe optically active aminophosphines and their use in enantioselective hydrosilylation. These ligands are prepared by condensation of 2-pyrrolecarbaldehyde or 2-acetylpyrrole with 1-phenylethylamine and, if appropriate, further reactions and may bear groups which are phosphonated on the pyrrole nitrogen.

WO 01/58589 describes compounds of phosphorus, arsenic and antimony based on diaryl-fused bicyclo[2.2.2] skeletons and catalysts in which these are present as ligands. In principle, hetaryl radicals may also be bound to the atom of main group V.

DE-A-100 23 471 describes a hydroformylation process using a hydroformylation catalyst comprising at least one phosphine ligand which contains two triarylphosphine groups, with at least one aryl radical of the two triarylphosphine groups being bound via a single bond to a nonaromatic 5- to 8-membered carbocyclic or heterocyclic bridging group. The phosphorus atoms may also bear, inter alia, hetaryl groups as further substituents.

The German patent application P 100 46 026.7 describes a hydroformylation process in which a complex based on a phosphorus-, arsenic- or antimony-containing compound as ligand is used as catalyst. This compound in each case has two groups containing a P-, As- or Sb atom and at least two further heteroatoms bound to a xanthene-like molecular skeleton.

U.S. Pat No. 5,710,344 relates to the hydroformylation of olefins by means of rhodium catalysts which have been modified with chelating phosphoric diamidite ligands having a bisphenol or bisnaphthol backbone and whose phosphorus atoms may bear unsubstituted pyrrolyl, imidazolyl or indolyl groups.

Gimbert et al., J. Org. Chem. 64, 3493 (1999) report cobalt complexes of N-methyl-bridged bispyrrolylphosphines and their use as reagents in the Pauson-Khand reaction.

Benincori et al. describe the preparation of 3,3'-dimethyl-1,1'-bis(diphenylphosphino)-2,2'-bisindole and a complex of this compound with palladium and also various physicochemical properties of these compounds.

Chiral catalyst systems comprising complexes of these compounds with a transition metal for carrying out stereocontroled reductions and isomerizations are disclosed in WO 96/01831.

EP-A 754 715 relates to complexes of alkylene-bridged di(pyrrolylphenylphosphines) with a group VIII metal and the use of these complexes as catalysts for preparing polyketones.

Van Leeuwen et al., Organometallics 19, 2504 (2000) describe the synthesis of phosphoric diamide chelating ligands which have a bisphenol or xanthene backbone and whose diamide unit is formed by biuret groups, and also the catalytic properties of the rhodium complexes of these compounds in hydroformylation.

WO 98/42716 relates to a method of synthesizing 2,2'-bisphosphino-1,1'-binaphthyl ligands whose phosphorus atoms bear pyrrolyl groups.

DE-A 199 13 352 relates to cyclic oxaphosphorins which are substituted on the phosphorus atom by pyrrole derivatives and to the use of these ligands in hydroformylation catalysts.

WO-A-99/52915 describes chiral phosphorus-containing ligands based on bicyclic compounds of carbocyclic and heterocyclic 5- and 6-atomic compounds. In these, the aromatic rings which form the bicycle are linked to one another by means of a single bond between two ring carbons.

WO 99/52632 relates to a process for hydrocyanation using phosphorus-containing chelating ligands having, inter alia, a 1,1'-bisphenol or 1,1'-bisnaphthol backbone in which the phosphorus atom may be substituted by pyrrole groups.

It is an object of the present invention to provide ligands which make it possible to hydroformylate relatively long-chain, terminal or internal olefins or industrial mixtures of olefins having terminal and internal double bonds, e.g. 1-butene/2-butene mixtures, to give aldehydes having a high linearity at a good conversion. Another object of the present invention is to provide an improved process for preparing 2-propylheptanol.

We have found that this object is achieved by pnicogen chelate compounds of the formula I

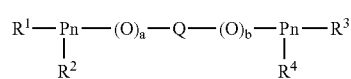

where
Q is a bridging group of the formula

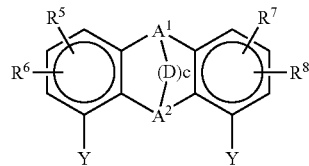

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl, $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ form an intramolecular bridging group D, D is a divalent bridging group selected from among the groups

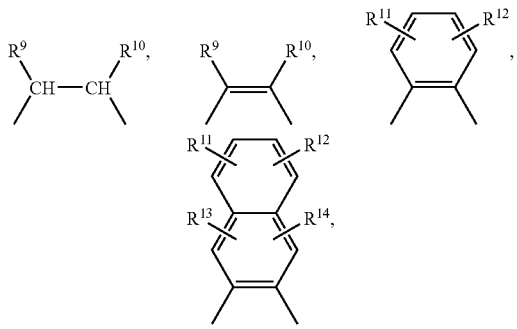

where $R^9$ and $R^{10}$ are each, independently of one another, hydrogen, alkyl, cycloalkyl, aryl, halogen, trifluoromethyl, carboxyl, carboxylate or cyano or are joined to one another to form a $C_3$–$C_4$-alkylene bridge, $R^{11}$, $R^{12}$, $R^{13}$ and $R^{14}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, acyl or nitro, c is 0 or 1, Y is a chemical bond, $R^5$, $R^6$, $R^7$ and $R^8$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1)_xR^f$, halogen, trifluoromethyl, nitro, acyl or cyano, where $R^f$, $E^1$, $E^2$ and $E^3$ are identical or different radicals selected from among hydrogen, alkyl, cycloalkyl and aryl, $R^g$ is hydrogen, methyl or ethyl, $M^+$ is a cation, $X^-$ is an anion and x is an integer from 1 to 120, or $R^5$ and $R^7$ together with two adjacent carbon atoms of the benzene ring to which they are bound form a fused ring system having 1, 2 or 3 further rings, a and b are each, independently of one another, 0 or 1, Pn is a pnicogen atom selected from among the elements phosphorus, arsenic or antimony, and $R^1$, $R^2$, $R^3$, $R^4$ are each, independently of one another, hetaryl, hetaryloxy, alkyl, alkoxy, aryl, aryloxy, cycloalkyl, cycloalkoxy, heterocycloalkyl, heterocycloalkoxy or an $NE^1E^2$ group, with the proviso that $R^1$ and $R^3$ are pyrrole groups bound via the nitrogen atom to the pnicogen atom Pn, or $R^1$ together with $R^2$ and/or $R^3$ together with $R^4$ form a divalent group E of the formula Py—I—W containing at least one pyrrole group bound via the pyrrole nitrogen to the pnicogen atom Pn, where Py is a pyrrole group, I is a chemical bond or O, S, $SiR^aR^b$, $NR^c$ or $CR^hR^i$, W is cycloalkyl, cycloalkoxy, aryl, aryloxy, hetaryl or hetaryloxy, and $R^h$ and $R^i$ are each, independently of one another, hydrogen, alkyl, cycloalkyl, heterocycloalkyl, aryl or hetaryl, or form a bispyrrole group of the formula Py—I—Py bound via the nitrogen atoms to the pnicogen atom Pn.

In a specific embodiment, the present invention provides pnicogen chelate compounds in which a substituted pyrrole group and/or a pyrrole group integrated into a fused ring system is covalently bound via its pyrrole nitrogen to the pnicogen atom.

In addition, the present invention provides catalysts comprising pnicogen chelate complexes with a metal of transition group VIII of the Periodic Table of the Elements comprising at least one pnicogen chelate compound of the formula I as ligand.

The present invention further provides a process for the hydroformylation of compounds containing at least one ethylenically unsaturated double bond, and especially a process for preparing aldehydes and/or alcohols by hydroformylation of $C_3$–$C_{20}$-olefins, preferably $C_4$–$C_{20}$-olefins, at superatmospheric pressure and elevated temperature by means of $CO/H_2$ mixtures in the presence of a metal complex of a metal of transition group VIII of the Periodic Table of the Elements homogeneously dissolved in the reaction medium as catalyst and free ligand, wherein the catalyst used is a pnicogen chelate complex and the free ligand used is a pnicogen chelate compound of the formula I.

The invention further provides a process for preparing 2-propylheptanol, which comprises the hydroformylation of butene, an aldol condensation of the resulting hydroformylation products and the subsequent hydrogenation of the condensation products, wherein a complex of a metal of transition group VIII with at least one pnicogen chelate compound of the formula I as ligand is used as hydroformylation catalyst.

In the explanations of the present invention, the expression 'alkyl' encompasses straight-chain and branched alkyl groups. These are preferably straight-chain or branched $C_1$–$C_{20}$-alkyl groups, more preferably $C_1$–$C_{12}$-alkyl groups, particularly preferably $C_1$–$C_8$-alkyl groups and very particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also encompasses substituted alkyl groups which may generally bear 1, 2, 3, 4 or 5, preferably 1, 2 or 3 and particularly preferably 1, substituent(s) selected from among the groups cycloalkyl, aryl, hetaryl, halogen, $NE^1E^2$, $NE^1E^2E^{3+}$, carboxyl, carboxylate, —$SO_3H$ and sulfonate.

For the purposes of the present invention, the expression "alkylene" refers to straight-chain or branched alkanediyl groups having from 1 to 4 carbon atoms.

For the purposes of the present invention, the expression "cycloalkyl" encompasses both unsubstituted and substituted cycloalkyl groups, preferably $C_5$–$C_7$-cycloalkyl groups such as cyclopentyl, cyclohexyl or cycloheptyl, which, if they are substituted, may generally bear 1, 2, 3, 4 or 5, preferably 1, 2 or 3 and particularly preferably 1, substituent(s) selected from among the groups alkyl, alkoxy and halogen.

For the purposes of the present invention, the expression "heterocycloalkyl" encompasses saturated cycloaliphatic groups generally having from 4 to 7, preferably 5 or 6, ring atoms, in which 1 or 2 of the ring carbons are replaced by heteroatoms selected from among the elements oxygen, nitrogen and sulfur and which may be substituted. If they are substituted, these heterocycloaliphatic groups may bear 1, 2 or 3, preferably 1 or 2, particularly preferably 1, substituent(s) selected from among alkyl, aryl, $COOR^f$, $COO^-M^+$ and $NE^1E^2$, preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

For the purposes of the present invention, the expression "aryl" encompasses both unsubstituted and substituted aryl groups and preferably refers to phenyl, tolyl, xylyl, mesityl, naphthyl, fluorenyl, anthracenyl, phenanthrenyl or naphthacenyl, particularly preferably phenyl or naphthyl, where, if they are substituted, these aryl groups may generally bear 1, 2, 3, 4 or 5, preferably 1, 2 or 3 and particularly preferably 1, substituent(s) selected from among the groups alkyl, alkoxy, carboxyl, carboxylate, trifluoromethyl, —$SO_3H$, sulfonate, $NE^1E^2$, alkylene-$NE^1E^2$, nitro, cyano and halogen.

For the purposes of the present invention, the expression "hetaryl" encompasses unsubstituted or substituted heteroaromatic groups, preferably the groups pyridyl, quinolinyl, acridinyl, pyridazinyl, pyrimidinyl, pyrazinyl, and the subgroup of "pyrrol groups". If they are substituted, these heteroaromatic groups may generally bear 1, 2 or 3 substituents selected from among the groups alkyl, alkoxy, carboxyl, carboxylate, —$SO_3H$, sulfonate, $NE^1E^2$, alkylene-$NE^1E^2$, trifluoromethyl and halogen.

For the purposes of the present invention, the expression "pyrrol group" refers to a series of unsubstituted or substituted heteroaromatic groups which are structurally derived from the pyrrol skeleton and whose heterocycle contains a pyrrolic nitrogen atom which can be covalently bound to other atoms, for example a pnicogen atom. The expression "pyrrol group" thus encompasses the unsubstituted or substituted groups pyrrolyl, imidazolyl, pyrazolyl, indolyl, purinyl, indazolyl, benzotriazolyl, 1,2,3-triazolyl, 1,3,4-triazolyl and carbazolyl, which, if they are substituted, may generally bear 1, 2 or 3, preferably 1 or 2, particularly preferably 1, substituent(s) selected from among the groups alkyl, alkoxy, acyl, carboxyl, carboxylate, —$SO_3H$, sulfonate, $NE^1E^2$, alkylene-$NE^1E^2$, trifluoromethyl and halogen.

The expression "bispyrrole group" accordingly encompasses, for the purposes of the present invention, divalent groups of the formula Py—I—Py, which comprise two pyrrole groups joined by a direct chemical bond or via alkylene, oxa, thio, imino, silyl or alkylimino groups, for example the bisindolediyl group of the formula

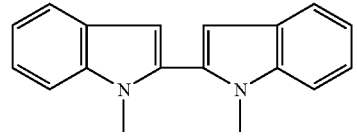

as an example of a bispyrrole group which comprises two directly linked pyrrole groups, in this case indolyl, or the bispyrrolediylmethane group of the formula

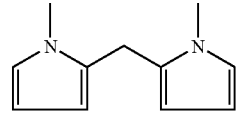

as an example of a bispyrrole group which comprises two pyrrole groups, in this case pyrrolyl, connected via a methylene group. Like the pyrrole groups, the bispyrrole groups can also be unsubstituted or substituted and, if they are substituted, may generally bear 1, 2 or 3, preferably 1 or 2, in particular 1, substituent(s) selected from among alkyl, alkoxy, carboxyl, carboxylate, —$SO_3H$, sulfonate, $NE^1E^2$, alkylene-$NE^1E^2$, trifluoromethyl and halogen per pyrrole unit. In these indications of the number of possible substituents, the linking of the pyrrole units by a direct chemical bond or via the abovementioned groups is not regarded as substitution.

For the purposes of the present invention, carboxylate and sulfonate are preferably a derivative of a carboxylic acid function or a sulfonic acid function, in particular a metal carboxylate or sulfonate, a carboxylic ester or sulfonic ester function or a carboxamide or sulfonamide function. Substituents of this type include, for example, esters with $C_1$–$C_4$-alkanols, e.g. methanol, ethanol, n-propanol, isopropanol, n-butanol, sec-butanol and tert-butanol.

The above explanations of the expressions "alkyl", "cycloalkyl", "aryl", "heterocycloalkyl" and "hetaryl" apply analogously to the expressions "alkoxy", "cycloalkoxy", "aryloxy", "heterocycloalkoxy" and "hetaryloxy".

For the purposes of the present invention, the expression "acyl" refers to alkanoyl or aroyl groups generally having from 2 to 11, preferably from 2 to 8, carbon atoms, for example the acetyl, propionyl, butyryl, pentanoyl, hexanoyl, heptanoyl, 2-ethylhexanoyl, 2-propylheptanoyl, benzoyl or naphthoyl group.

The groups $NE^1E^2$ and $NE^4E^5$ are preferably N,N-dimethylamino, N,N-diethylamino, N,N-dipropylamino, N,N-diisopropylamino, N,N-di-n-butylamino, N,N-di-tert-butylamino, N,N-dicyclohexyl-amino or N,N-diphenylamino.

Halogen is fluorine, chlorine, bromine or iodine, preferably fluorine, chlorine or bromine.

$M^+$ is a cation equivalent, i.e. a monovalent cation or that part of a polyvalent cation which corresponds to a single positive charge. The cation $M^+$ serves merely as counterion for balancing negatively charged substituent groups, e.g. the $COO^-$ group or the sulfonate group, and can in principle be chosen at will. Preference is therefore given to using alkali metal ions, in particular Na$^+$, K$^+$, Li$^+$ ions, or onium ions, e.g. ammonium, monoalkylammonium, dialkylammonium, trialkylammonium, tetraalkylammonium, phosphonium, tetraalkylphosphonium or tetraarylphosphonium ions.

Analogous considerations apply to the anion equivalent X$^-$ which merely serves as counterion to positively charged substituent groups such as ammonium groups and can be chosen at will from among monovalent anions and parts of polyvalent anions corresponding to single negative charges. In general, preference is given to halide ions X$^-$, in particular chloride and bromide.

x is an integer from 1 to 240, preferably an integer from 3 to 120.

Fused ring systems can comprise aromatic, hydroaromatic and cyclic compounds joined by fusion. Fused ring systems have two, three or more than three rings. Depending on the way in which the rings of fused ring systems are joined, a distinction is made between ortho-fusion, i.e. each ring shares an edge, viz. two atoms, with each neighboring ring, and peri-fusion in which one carbon atom belongs to more than two rings. Among fused ring systems, preference is given to ortho-fused ring systems.

Y is a chemical bond, i.e. the linkage point of the bridging group Q to the groups —O— or, in the case of a and/or b being equal to 0, to the groups PnR$^1$R$^2$ or PnR$^3$R$^4$.

In the bridging group Q, the groups A$^1$ and A$^2$ are each, independently of one another, O, S, SiR$^a$R$^b$, NR$^c$ or CR$^d$R$^e$, where the substituents R$^a$, R$^b$ and R$^c$ may each be, independently of one another, hydrogen, alkyl, cycloalkyl, heterocycloalkyl, aryl or hetaryl, while the groups R$^d$ and R$^e$ are each, independently of one another, hydrogen, alkyl, cycloalkyl, heterocycloalkyl, aryl or hetaryl or the group R$^d$ together with a further group R$^d$ or the Group R$^e$ together with a further group R$^e$ may form an intramolecular bridging group D.

D is a divalent bridging group which is selected from among the groups

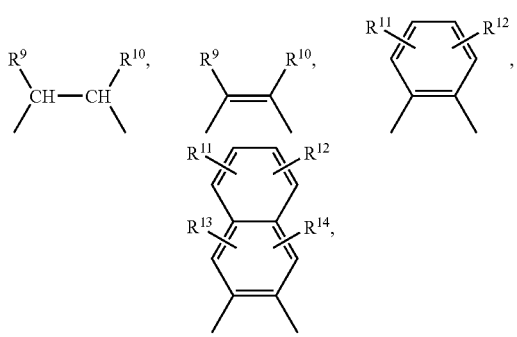

where R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$–C$_4$-alkylene group and R$^{11}$, R$^{12}$, R$^{13}$ and R$^{14}$ may each be, independently of one another, hydrogen, alkyl, cycloalkyl, aryl, halogen, trifluoromethyl, COOH, carboxylate, cyano, alkoxy, SO$_3$H, sulfonate, NE$^1$E$^2$, alkylene-NE$^1$E$^2$E$^3$$^+$X$^-$, aryl or nitro. The groups R$^9$ and R$^{10}$ are each preferably hydrogen, C$_1$–C$_{10}$-alkyl or carboxylate and the groups R$^{11}$, R$^{12}$, R$^{13}$ and R$^{14}$ are preferably each hydrogen, C$_1$–C$_{10}$-alkyl, halogen, in particular fluorine, chlorine or bromine, trifluoromethyl, C$_1$–C$_4$-alkoxy, carboxylate, sulfonate or C$_1$–C$_8$-aryl. Preference is given to R$^9$, R$^{10}$, R$^{11}$, R$^{12}$, R$^{13}$ and R$^{14}$ each being hydrogen. For use in an aqueous reaction medium, preference is given to pnicogen chelate compounds in which 1, 2 or 3, preferably 1 or 2, in particular 1, of the groups R$^{11}$, R$^{12}$, R$^{13}$ and/or R$^{14}$ are a COO$^-$Me$^+$, a SO$_3$$^-$M$^+$ or a NE$^1$E$^2$E$^3$$^+$X$^-$ group, where M$^+$ and X$^-$ are as defined above.

Particularly preferred bridging groups D are the ethylene group

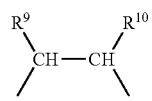

and the 1,2-phenylene group

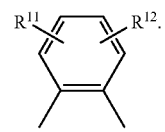

When R$^d$ together with a further group R$^d$ or R$^e$ together with a further group R$^e$ forms an intramolecular bridging group D, i.e. the index c is equal to 1, it follows that both A$^1$ and A$^2$ each have to be a CR$^d$R$^e$ group and the bridging group Q has a triptycene-like carbon skeleton.

Preferred bridging groups Q also include, apart from those having a triptycene-like carbon skeleton, those in which the index c is 0 and the groups A$^1$ and A$^2$ are selected from among the groups O, S and CR$^d$R$^e$, in particular from among O, S, the methylene group (R$^d$=R$^e$=H), the dimethylmethylene group (R$^d$=R$^e$=CH$_3$), the di-n-propylmethylene group (R$^d$=R$^e$=n-propyl) and the di-n-butylmethylene group (R$^d$=R$^e$=n-butyl). Particular preference is given to bridging groups Q in which A$^1$ is different from A$^2$, in which case A$^1$ is preferably a CR$^d$R$^e$ group and A$^2$ is preferably an O or S atom, particularly preferably O.

Particularly preferred bridging groups Q are thus ones which have a triptycene-like or xanthene-like (A$^1$:CR$^d$R$^e$, A$^2$:O) skeleton.

The substituents R$^5$, R$^6$, R$^7$ and R8 generally each hydrogen, alkyl, cycloalkyl, heterocycloalkyl, aryl or hetaryl. R$^5$ and R$^7$ are preferably each hydrogen and R$^6$ and R$^8$ are preferably each C$_1$–C$_4$-alkyl, e.g. methyl, ethyl, n-propyl, n-butyl or tert-butyl. It goes without saying that the positions of the phenyl rings of the bridging group Q which are not occupied by substituents bear a hydrogen atom.

Since the substituents R$^5$, R$^6$, R$^7$ and R$^8$ generally make virtually no contribution to the catalytic activity of the catalysts prepared from the pnicogen chelate ligands, apart from having an influence on the solubility, R$^5$, R$^6$, R$^7$ and R$^8$ are preferably each hydrogen.

If R$^5$ and/or R$^7$ form a fused-on ring system, the rings are preferably benzene or naphthalene rings. Fused-on benzene rings are preferably unsubstituted or bear 1, 2 or 3, in particular 1 or 2, substituents selected from among alkyl, alkoxy, halogen, SO$_3$H, sulfonate, NE$^1$E$^2$, alkylene-NE$^1$E$^2$, trifluoromethyl, nitro, COOR$^f$, alkoxycarbonyl, acyl and cyano. Fused-on naphthalene rings are preferably unsubstituted or bear a total of 1, 2 or 3, in particular 1 or 2, of the substituents mentioned above for the fused-on benzene rings in the ring which is not fused on and/or in the fused-on ring.

If use of the pnicogen chelate compounds of the present invention in an aqueous hydroformylation medium is envisaged, at least one of the radicals $R^5$, $R^6$, $R^7$ and $R^8$ is a polar (hydrophilic) group, which then generally results in water-soluble pnicogen chelate complexes with a group VIII metal. The polar groups are preferably selected from among $COOR^f$, $COO^-M^+$, $SO_3R^f$, $SO_3^-M^+$, $NE^1E^2$, alkylene-$NE^1E^2$, $NE^1E^2E^{3+}X^-$, alkylene-$NE^1E^2E^{3+}X^-$, $OR^f$, $SR^f$, $(CHR^gCH_2O)_xR^f$ or $(CH_2CH_2N(E^1))_xR^f$, where $R^f$, $E^1$, $E^2$, $E^3$, $R^g$, $M^+$, $X^-$ and x are as defined above.

The bridging group Q is bound to the groups $PnR^1R^2$ and $PnR^3R^4$ via the chemical bond Y either directly or via an oxygen atom O.

Pn is an atom of the pnicogen group selected from among phosphorus, arsenic and antimony. Pn is particularly preferably phosphorus.

The individual pnicogen atoms Pn of the pnicogen chelate compounds of the present invention are each bound via two covalent bonds to two substituents $R^1$ and $R^2$ or $R^3$ and $R^4$, where the substituents $R^1$, $R^2$, $R^3$ and $R^4$ may each be, independently of one another, hetaryl, hetaryloxy, alkyl, alkoxy, aryl, aryloxy, cycloalkyl, cycloalkoxy, heterocycloalkyl, heterocycloalkoxy or an $NE^1E^2$ group, with the proviso that $R^1$ and $R^3$ are pyrrole groups bound via the pyrrole nitrogen to the pnicogen atom Pn. The substituents $R^2$ and/or $R^4$ are advantageously also pyrrole groups bound via the pyrrole nitrogen to the pnicogen atom Pn. Furthermore, the substituent $R^1$ together with the substituent $R^2$ or the substituent $R^3$ together with the substituent $R^4$ or the substituent $R^1$ together with the substituent $R^2$ and the substituent $R^3$ together with the substituent $R^4$ can advantageously form a bispyrrole group bound via the pyrrole nitrogens to the pnicogen atom Pn.

The meanings of the individual expressions used in the previous paragraph correspond to the definitions given earlier in the present text.

In a further advantageous embodiment of the present invention, the substituent $R^1$ together with the substituent $R^2$ or the substituent $R^3$ together with the substituent $R^4$ or the substituent $R^1$ together with the substituent $R^2$ and the substituent $R^3$ together with the substituent $R^4$ can form a divalent group of the formula Py—I—W containing at least one pyrrole group bound via the pyrrole nitrogen to the pnicogen atom Pn,
where Py is a pyrrole group,
I is a chemical bond or O, S, $SiR^aR^b$, $NR^c$ or $CR^hR^i$,
W is cycloalkyl, cycloalkoxy, aryl, aryloxy, hetaryl or hetaryloxy,
and
$R^h$ and $R^i$ are each, independently of one another, hydrogen, alkyl, cycloalkyl, heterocycloalkyl, aryl or hetaryl,
where the terms employed here are as defined earlier in the present text.

Preferred divalent groups of the formula

Py—I—W are, for example:

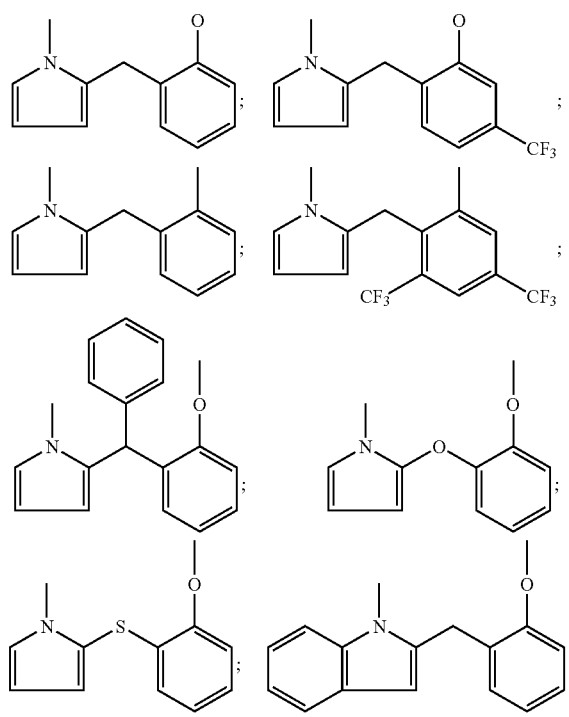

Merely for the purpose of illustrating the pnicogen chelate compound of the present invention, some advantageous compounds are listed below:

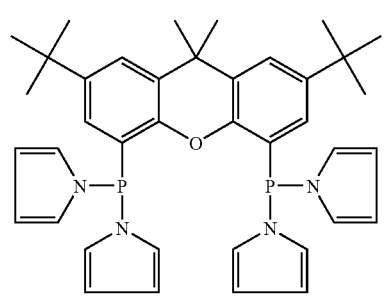

1

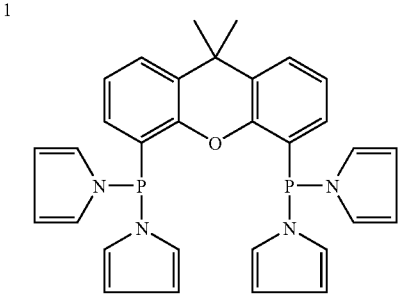

2

-continued
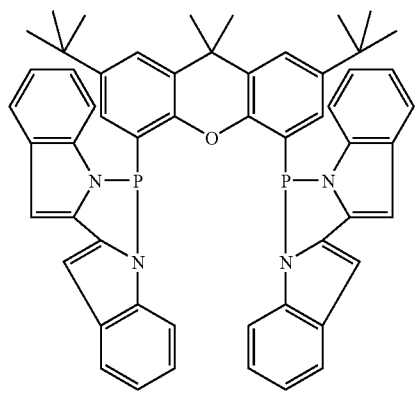
3
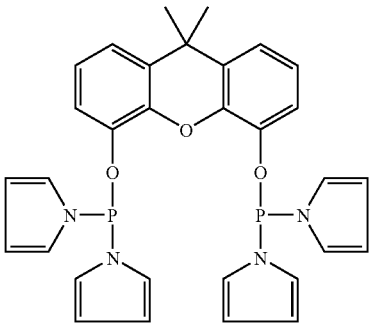
4
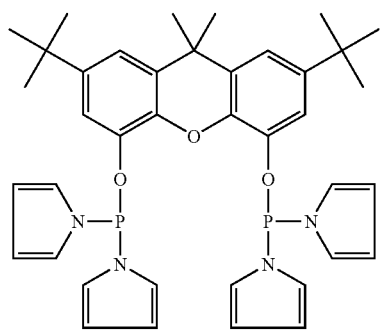
5
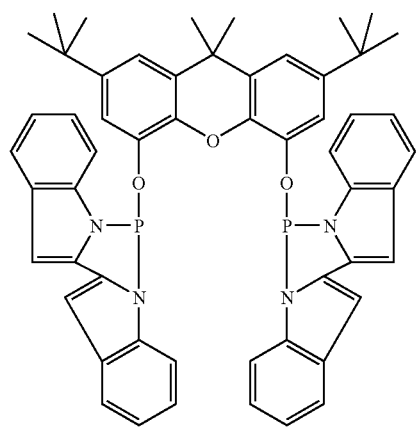
6
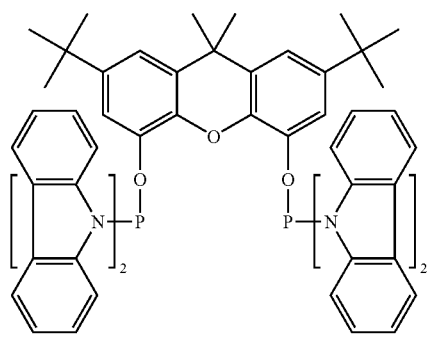
7
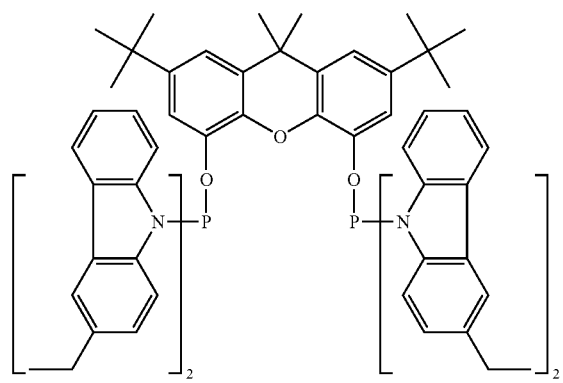
8
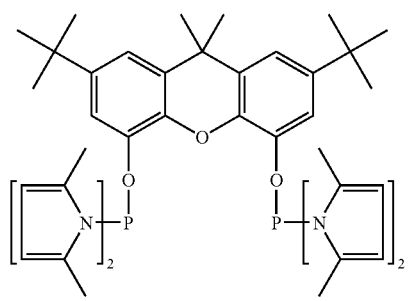
9

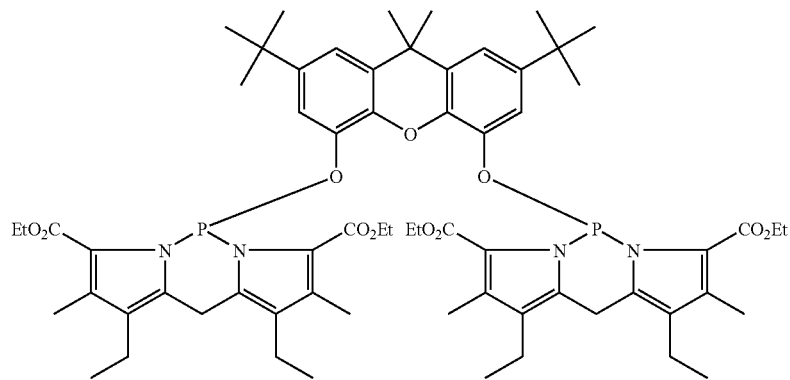
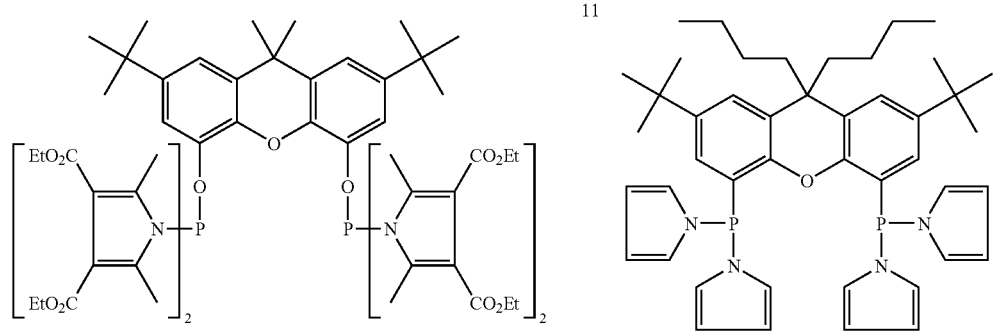
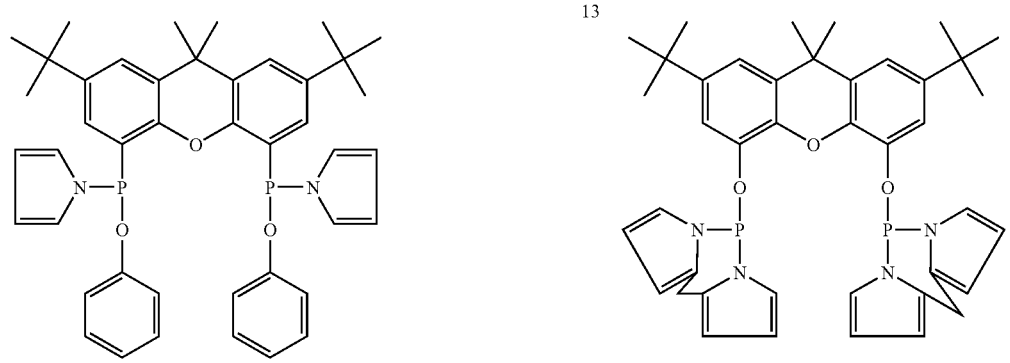
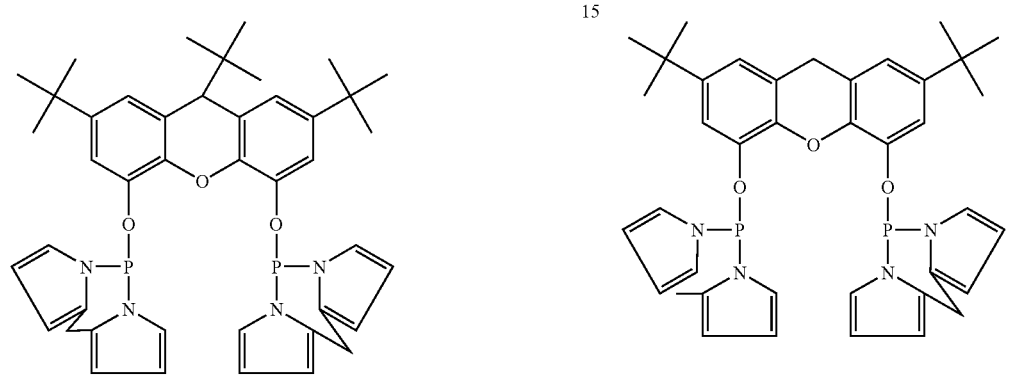

-continued
17
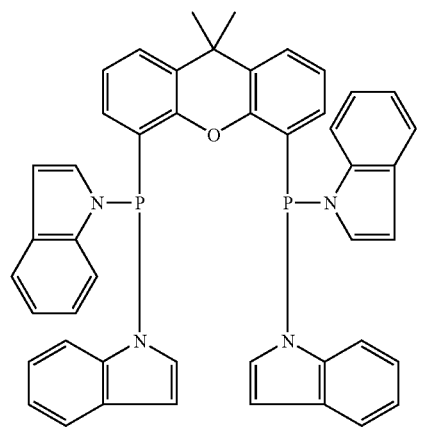
18
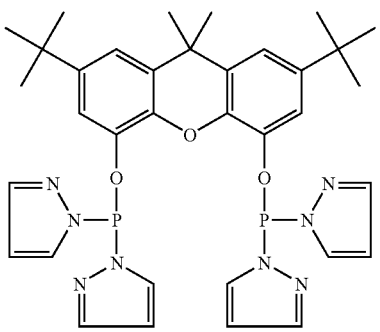
19
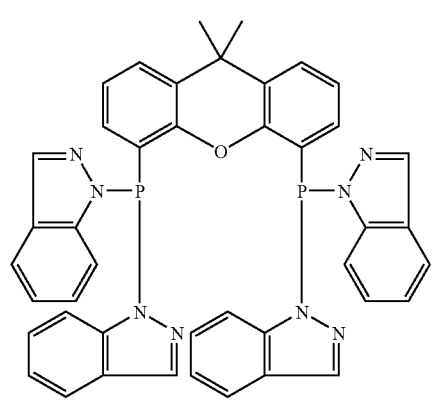
20
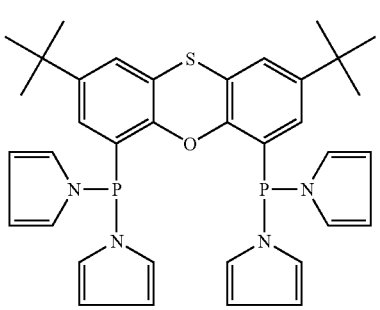
21
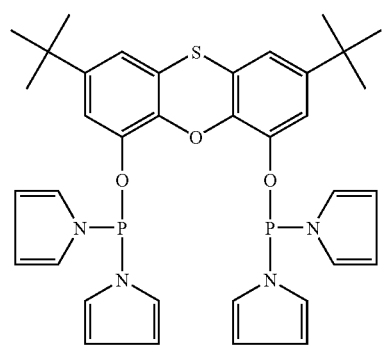
22
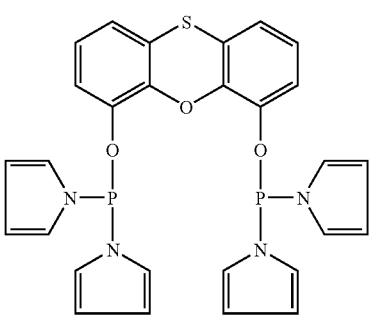
23
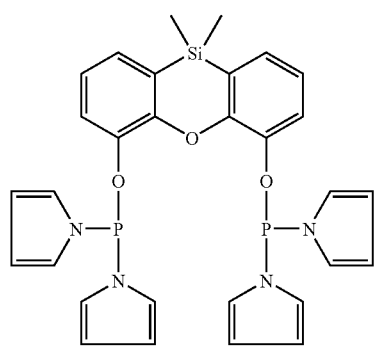
24
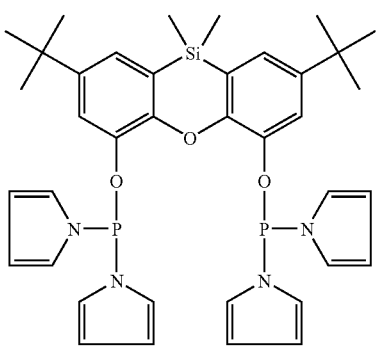

-continued
25
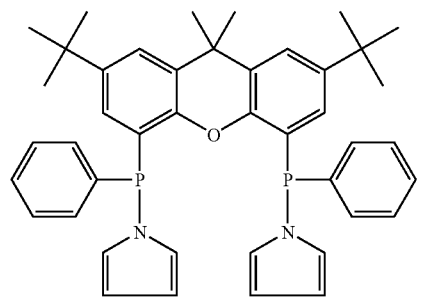
26
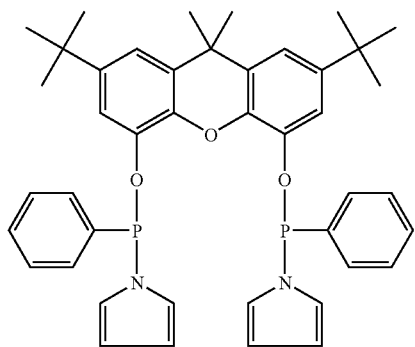
27
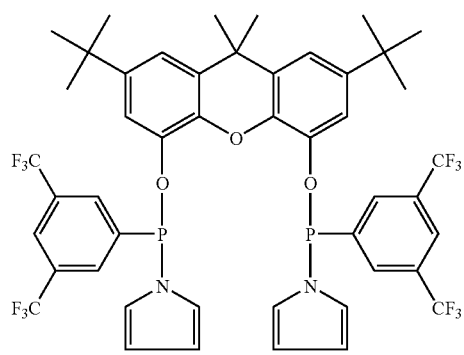
28
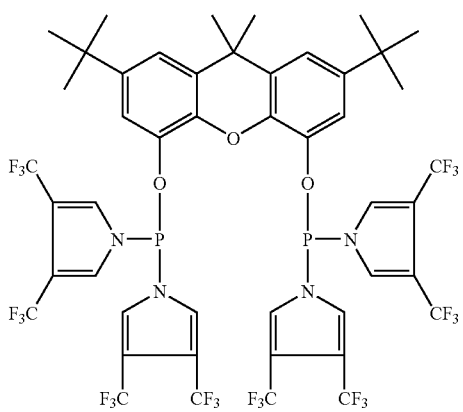
29
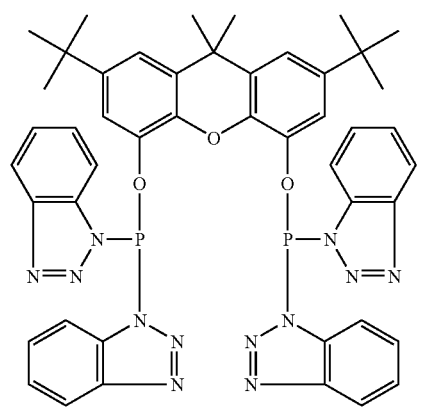
30
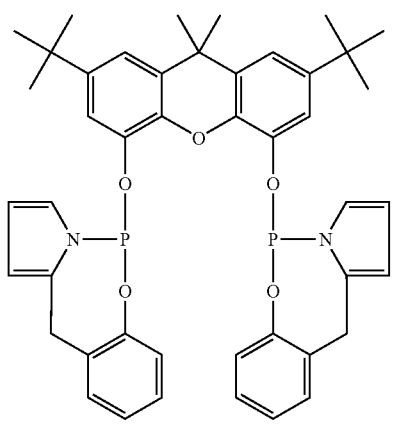
31
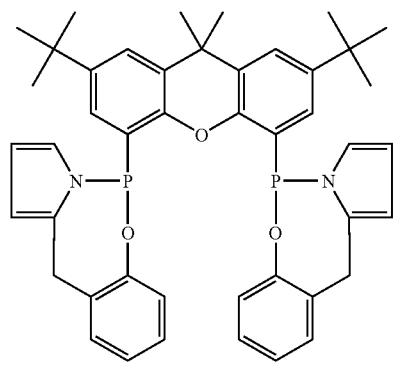
32
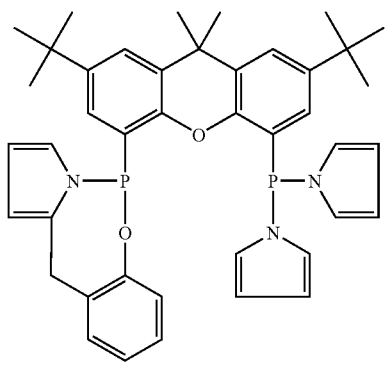

-continued
33
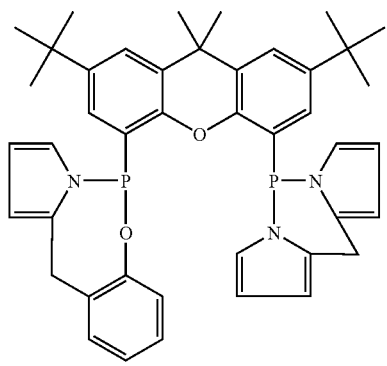
34
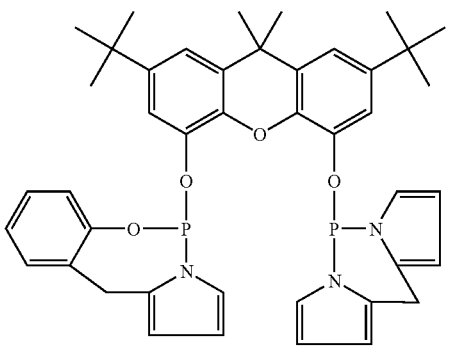
35
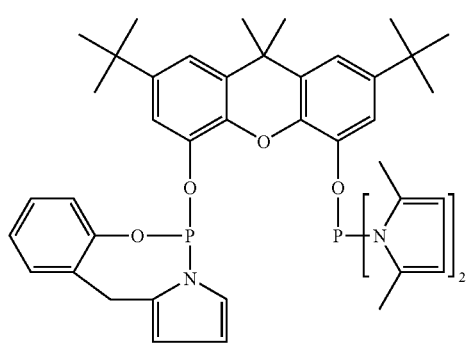
36
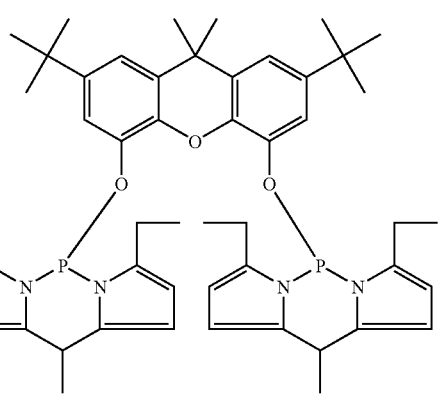
37
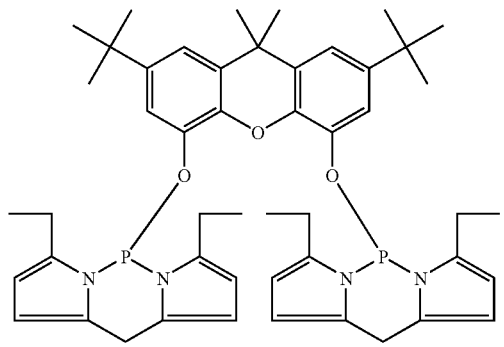
38
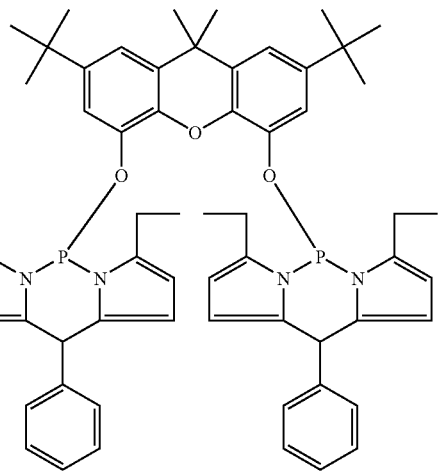
39
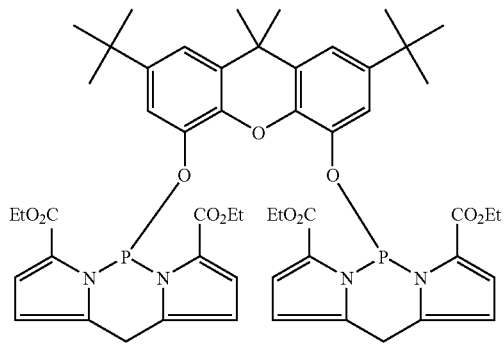
40
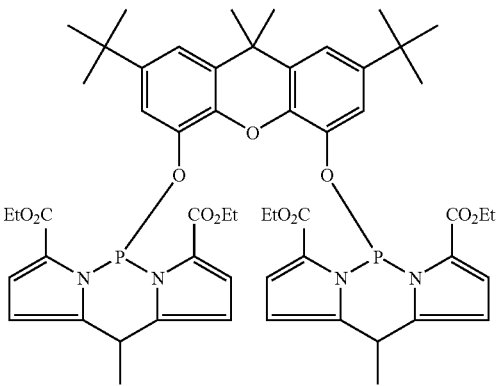

-continued
41
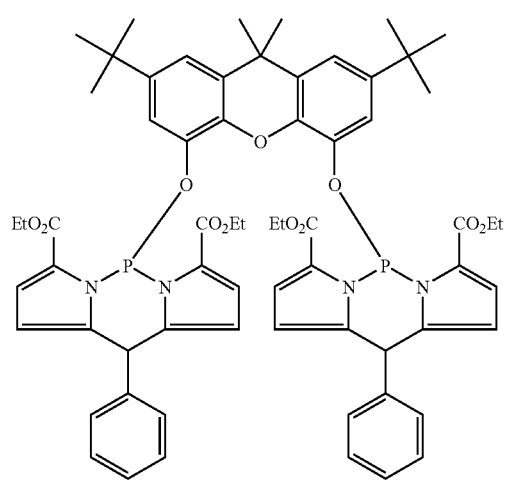
42
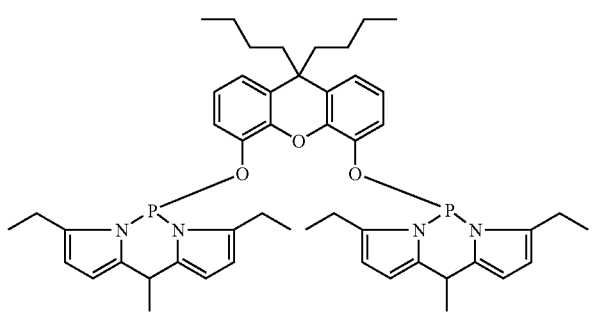
43
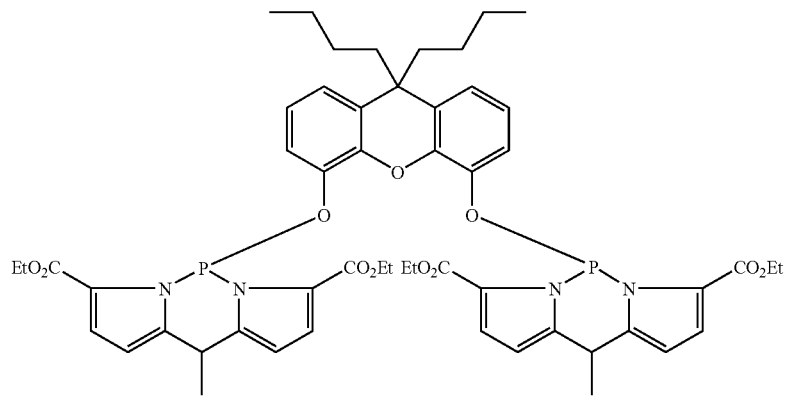
44
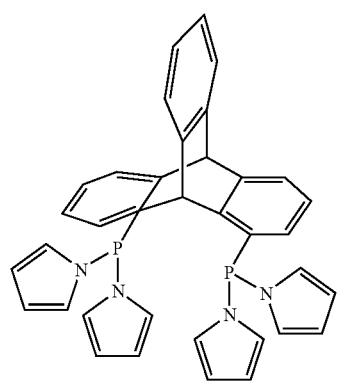
45
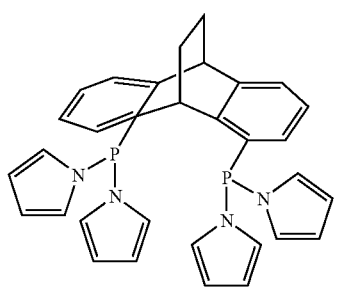

-continued

46

47

Et:ethyl

In a preferred embodiment, the pnicogen chelate compounds of the present invention and those used according to the present invention are selected from among compounds of the formula II $$R^{19}-(O)_a\diagdown_{Pn}\diagup(O)_b-Q-(O)_a\diagdown_{Pn}\diagup(O)_b-R^{20} \quad (II)$$

where
$R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^1$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, where
W' is a single bond, a heteroatom or a divalent bridging group having from 1 to 20 bridge atoms,
$R^k$, $E^4$, $E^5$, $E^6$ are identical or different radicals selected from among hydrogen, alkyl, cycloalkyl and aryl,
$R^1$ is hydrogen, methyl or ethyl,
$M^+$ is a cation equivalent,
$X^-$ is an anion equivalent and
y is an integer from 1 to 240,
where two adjacent radicals $R^{15}$, $R^{16}$, $R^{17}$ and $R^{18}$ together with the carbon atom of the pyrrole ring to which they are bound may also form a fused ring system having 1, 2 or 3 further rings,
with the proviso that at least one of the radicals $R^{15}$, $R^{16}$, $R^{17}$ and $R^{18}$ is not hydrogen and that $R^{19}$ and $R^{20}$ are not joined to one another,
$R^{19}$ and $R^{20}$ are each, independently of one another cycloalkyl, heterocycloalkyl, aryl or hetaryl,
a and b are each, independently of one another 0 or 1,
Pn is a pnicogen atom selected from among the elements phosphorus, arsenic or antimony, preferably phosphorus, Q is a bridging group of the formula where
$A^1$ and $A^2$ are each, independently of one another, O, S, SiR$^a$R$^b$, NR$^c$ or CR$^d$R$^e$, where
$R^a$, $R^b$ and $R^c$ are each, independently of one another, hydrogen, alkyl, cycloalkyl, heterocycloalkyl, aryl or hetaryl,
$R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ form an intramolecular bridging group D,
D is a divalent bridging group selected from among the groups where
$R^9$ and $R^{10}$ are each, independently of one another, hydrogen, alkyl, cycloalkyl, aryl, halogen, trifluoromethyl, carboxyl, carboxylate or cyano or are joined to one another to form a $C_3$–$C_4$-alkylene bridge, $R^{11}$, $R^{12}$, $R^{13}$ and $R^{14}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, acyl or nitro, c is 0 or 1, $R^5$, $R^6$, $R^7$ and $R^8$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano, where $R^f$, $E^1$, $E^2$ and $E^3$ are identical or different radicals selected from among hydrogen, alkyl, cycloalkyl and aryl, $R^g$ is hydrogen, methyl or ethyl, $M^+$ is a cation, $X^-$ is an anion and x is an integer from 1 to 120, or $R^5$ and/or $R^7$ together with two adjacent carbon atoms of the benzene ring to which they are bound form a fused ring system having 1, 2 or 3 further rings.

In the compounds of the formula II, the pnicogen atoms Pn are preferably both phosphorus.

As regards suitable and preferred embodiments of the bridging group Q, all that which has been said above is hereby incorporated by reference at this point.

The radicals $R^{15}$ to $R^{18}$ can have, independently of one another, identical or different meanings.

Preference is given to compounds of the formula II in which one or two of the radicals $R^{15}$, $R^{16}$, $R^{17}$ and $R^{18}$ in each of the pyrrole groups are one of the abovementioned substituents other than hydrogen and the remainder are hydrogen. Preference is also given to compounds of the formula II in which the pyrrole groups bear a substituent other than hydrogen in the 2 position, the 2,5 positions or the 3,4 positions.

The substituents $R^{15}$ to $R^{18}$ which are not hydrogen are preferably selected independently from among $C_1$–$C_8$-alkyl, preferably $C_1$–$C_4$-alkyl, especially methyl, ethyl, isopropyl and tert-butyl, alkoxycarbonyl, such as methoxycarbonyl, ethoxycarbonyl, isopropyloxycarbonyl and tert-butyloxycarbonyl and trifluoromethyl.

Preference is given to compounds of the formula I in which the radicals $R^{15}$ and $R^{16}$ and/or $R^{17}$ and $R^{18}$ together with the carbon atoms of the pyrrole ring to which they are bound form a fused ring system having 1, 2 or 3 further rings. If $R^{15}$ and $R^{16}$ and/or $R^{17}$ and $R^{18}$ form a fused-on ring system, the fused-on systems are preferably benzene or naphthalene units. Fused-on benzene rings are preferably unsubstituted or bear 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, $COOR^k$, alkoxycarbonyl, acyl and cyano. Fused-on naphthalene units are preferably unsubstituted or bear 1, 2 or 3, in particular 1 or 2, of the substituents mentioned above in the case of the fused-on benzene rings in the ring which is not fused on and/or in the fused-on ring. If $R^{15}$ and $R^{16}$ form a fused-on ring system, $R^{17}$ and $R^{18}$ are preferably both hydrogen or $R^{18}$ is hydrogen and $R^{17}$ is a substituent selected from among $C_1$–$C_8$-alkyl, preferably $C_1$–$C_4$-alkyl, especially methyl, ethyl, isopropyl and tert-butyl.

If the compounds of the formula II are to be used in an aqueous hydroformylation medium, at least one of the radicals $R^{15}$, $R^{16}$, $R^{17}$ and/or $R^{18}$ is a polar (hydrophilic) group, so that complex formation with a group VIII metal then generally results in water-soluble complexes. The polar groups are preferably selected from among $COOR^k$, $COO^-$ $M^+$, $SO_3R^k$, $SO_3^{31}$ $M^+$, $NE^4E^5$, alkylene-$NE^4E^5$, $NE^4E^5E^{6+}$ $X^-$, alkylene-$NE^4E^5E^{6+}X^-$, $OR^k$, $SR^k$, $(CHR^1CH_2O)_yR^k$ or $(CH_2CH_2N(E^4))_yR^k$, where $R^k$, $E^4$, $E^5$, $E^6$, $R^1$, $M^+$, $X^-$ and y are as defined above.

The compounds of the formula II are preferably selected from among compounds of the formulae II.1 to II.3

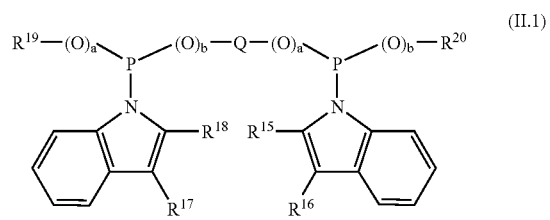

(II.1)

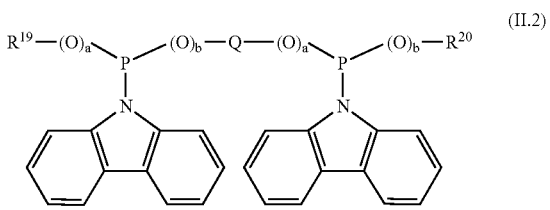

(II.2)

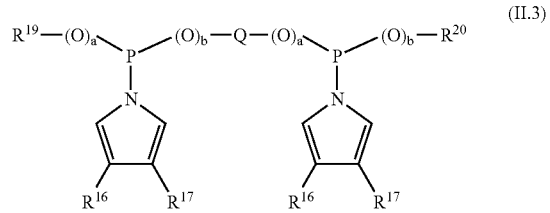

(II.3)

where $R^{15}$, $R^{16}$, $R^{17}$, $R^{18}$, Q, a and b are as defined above, where, in the formula II.3, at least one of the radicals $R^{16}$ and $R^{17}$ is not hydrogen, $R^{19}$ and $R^{20}$ are each, independently of one another, cycloalkyl, heterocycloalkyl, aryl or hetaryl.

In the compounds of the formula II.1, the radicals $R^{15}$ to $R^{18}$ are preferably all hydrogen. Compounds in which $R^{15}$ and $R^{18}$ are hydrogen and $R^{16}$ and $R^{17}$ are selected from among $C_1$–$C_8$-alkyl, preferably $C_1$–$C_4$-alkyl such as methyl, ethyl, isopropyl and tert-butyl, are also preferred.

In the compounds of the formula II.3, the radicals $R^{16}$ and $R^{17}$ are preferably selected from among $C_1$–$C_8$-alkyl, particularly preferably $C_1$–$C_4$-Alkyl such as methyl, ethyl, isopropyl and tert-butyl, and $COOR^k$, where $R^k$ is $C_1$–$C_4$-alkyl such as methyl, ethyl, isopropyl or tert-butyl.

Merely by way of illustration, some compounds of the formula II are listed below:
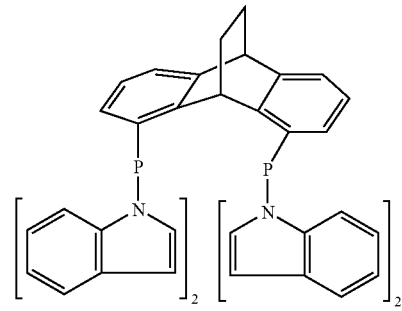
I
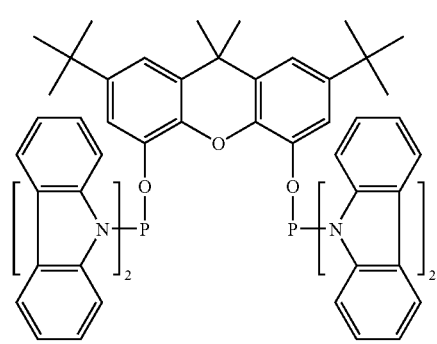
II
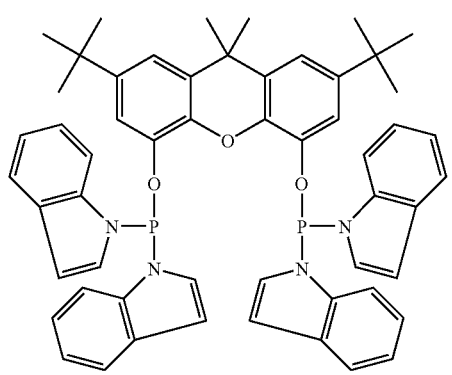
III
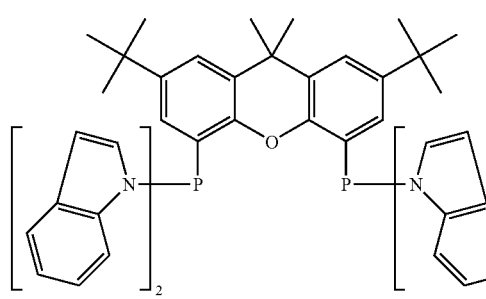
IV
-continued
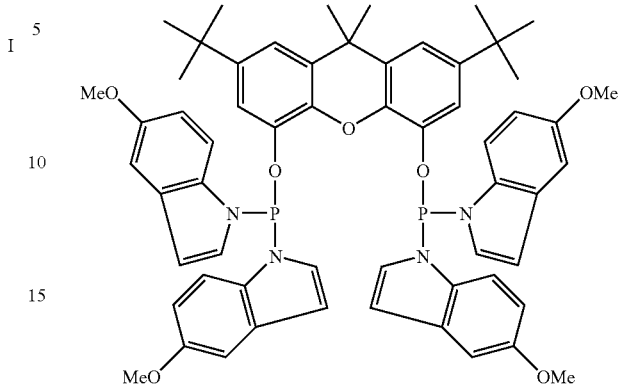
V
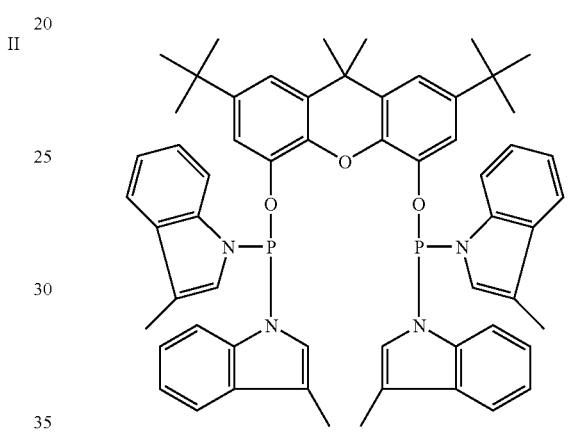
VI
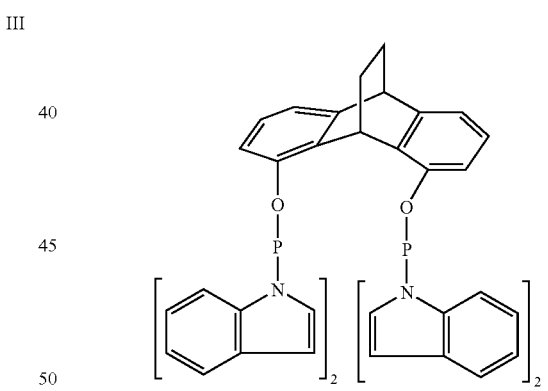
VII
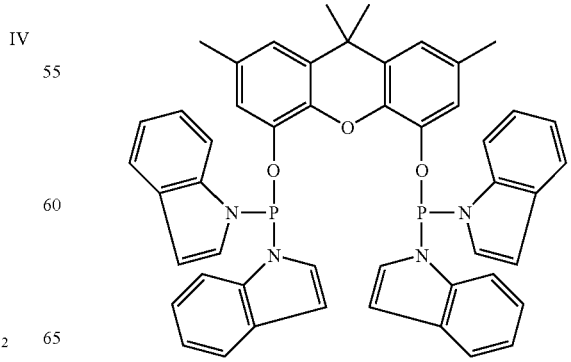
VIII -continued

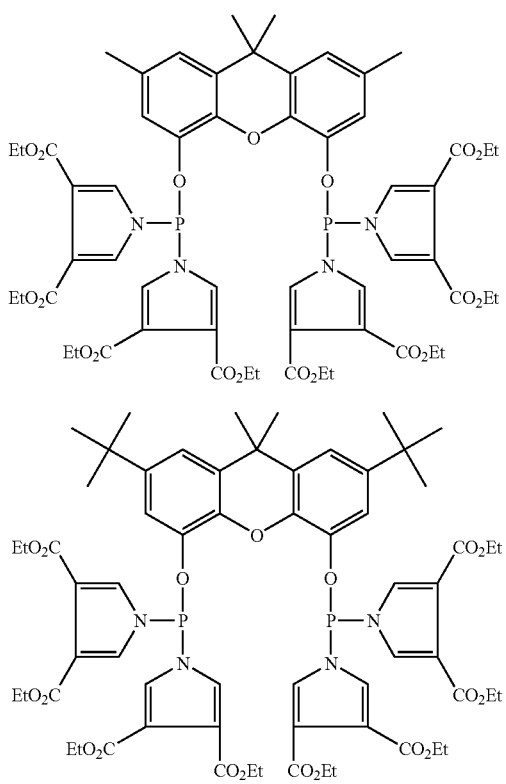

Me=methyl,
Et=ethyl,
$R^m$=H, carboxylate,
$R^n$=H, carboxylate.

The preparation of the pnicogen chelate compounds of the present invention advantageously starts out from compounds of the formula III

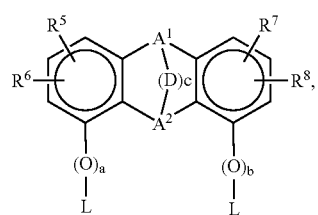

where $A^1$, $A^2$, D, $R^5$, $R^6$, $R^7$, $R^8$, a, b and c are as defined above and L is a leaving group which, when a and b are 0, may be, for example, hydrogen (when $A^2$ is oxygen), halogen, in particular fluorine, chlorine, bromine, $SO_3Me$ where Me=hydrogen or an alkali metal, in particular Li, Na or K, or, when a and b are 1, can be, for example, hydrogen, $C(O)CF_3$, $SO_2CH_3$, $SO_2$-tolyl or $SO_2CF_3$.

The starting compounds of the formula III in which a, b, c=0 can be prepared by the methods described by van Leuwen et al., Organometallics 14, 3081 (1995).

The starting compounds of the formula III in which a, b=1, c=0, and L=H can be obtained, for example, from the corresponding 1,8-dibromo compounds of the formula III (a, b=0; L=Br), e.g. by metalation using organometallic compounds of alkali metals, e.g. n-butyllithium, tert-butyllithium or the like, subsequent reaction with a borane, preferably $BH_3$, and oxidation of the resulting diborane compound by means of a peroxide, preferably hydrogen peroxide, in the presence of an aqueous alkali metal hydroxide, preferably lithium, sodium or potassium hydroxide.

To attach the groups $PnR^1R^2$ and $PnR^3R^4$, the starting compounds of the formula III are advantageously reacted with a halogen compound of the formula $HalPnR^1R^2$ or $HalPnR^3R^4$ in the presence of a base. Hal is preferably chlorine or bromine.

The compounds $HalPnR^1R^2$ and $HalPnR^3R^4$ can be obtained, for example, by a method analogous to that described by Petersen et al., J. Am. Chem. Soc. 117, 7696 (1995) by reacting the appropriate pyrrole compound, e.g. pyrrole, indole, benzotriazole, carbazole, 2,2'-dipyrrolylmethane, 2,2'-bisindole, with the appropriate pnicogen trihalide, e.g. phosphorus trichloride, in the presence of a tertiary amine, e.g. triethylamine, taking account of the stoichiometry of this reaction.

In an analogous procedure, it is possible, for example, to react the appropriate hydroxyarylpyrrolyl compounds with the pnicogen trihalide in the presence of a tertiary amine to give the corresponding starting compounds $HalPnR^1R^2$ or $HalPnR^3R^4$.

Further starting compounds $HalPnR^1R^2$ and $HalPnR^3R^4$ are obtainable by stepwise synthesis. Thus, for example, reaction of phenol with phosphorus trichloride in the presence of a tertiary amine, e.g. triethylamine, produces phenoxyphosphorus dichloride which can be reacted with one equivalent of the appropriate pyrrole compound, e.g. pyrrole, in the presence of a tertiary amine to give phenoxypyrrolylphosphorus chloride.

The preparation of the 2,2'-bisindole starting compounds can be carried out by a method analogous to those described in Tetrahedron 51, 5637 (1995) and Tetrahedron 51, 12801 (1995), and the preparation of the bis-2,2'-pyrrolylmethanes can be carried out as described in J. Org. Chem. 64, 1391 (1999) and the preparation of the 2'-pyrrolyl-o-phenoxymethanes can be carried out as described in J. Org. Chem. 46, 5060 (1981).

The starting compounds III having a triptycene-like carbon skeleton can be prepared in a known manner from the corresponding anthraquinone derivatives via the corresponding anthracene precursors (for preparation of these, see, for example: J. Org. Chem. 45, 1807 (1980); J. Org. Chem. 38, 1167 (1973); Bull Chem. Soc. Jm. 44, 1649 (1971); J. Am. Chem. Soc. 34, 3089 (1969); J. Org. Chem. 39, 770 (1974); Chem. Ber. 124, 333 (1991); J. Org. Chem. 51, 921 (1986)) by Diels-Alder reaction with the corresponding olefins, acetylenes or arynes. Information on carrying out these Diels-Alder reactions may be found in Chem. Ber. 119, 1016 (1986) and J.C.S. Chem. Comm. 961 (1999).

To prepare the pnicogen chelate compounds of the formulae I and II from the compounds of the formula III by reaction of the latter with the compounds $HalPnR^1R^2$ and $HalPnR^3R^4$, the compounds of the formula III firstly have to be activated.

In the case of compounds of the formula III in which a, b=0, this is advantageously carried out by metalation by means of an organometallic compound of an alkali metal, preferably an alkyllithium compound such as n-butyllithium, tert-butyllithium or methyllithium, with the leaving group L being replaced in a separate reaction by the corresponding alkali metal atom, preferably lithium.

After addition of HalPnR$^1$R$^2$ and HalPnR$^3$R$^4$ to this metalated compound, the corresponding pnicogen chelate compounds of the formula I or II in which a, b=0 are formed.

To activate the compounds of the formula III in which a, b=1, it is generally not necessary to employ a separate activation by means of organometallic alkali metal compounds. In general, the reaction of these compounds with the compounds HalPnR$^1$R$^2$ and HalPnR$^3$R$^4$ in the presence of a base, preferably a tertiary amine such as triethylamine or an alkali metal hydride or alkaline earth metal hydride, for example sodium hydride, potassium hydride or calcium hydride, leads directly to the novel pnicogen chelate compounds of the formula I or II in which a, b=0.

In place of compounds of the formula III (with a, b=0) in which L=halogen or SO$_3$Me, it is also possible to lithiate compounds III in which L=hydrogen and hydrogen, an alkoxy group or an alkoxycarbonyl group is in each case present in the meta position relative to A$^2$ (A$^2$=O or S). Such reactions are described in the literature as "ortho-lithiation" (cf., for example, D. W. Slocum, J. Org. Chem., 41, 3652–3654 (1976); J. M. Mallan, R. L. Bebb, Chem. Rev., 1969, 693ff; V. Snieckus, Chem. Rev., 1980, 6, 879–933). The organolithium compounds obtained in this way can then be reacted in the manner indicated above to form the chelate compounds of the formula I or II.

The arsenic and antimony compounds of the formula I or II can be prepared in an analogous manner.

In general, the catalysts or catalyst precursors used in each case are converted under hydroformylation conditions into catalytically active species of the formula H$_g$Z$_d$(CO)$_e$G$_f$, where Z is a metal of transition group VIII, G is a phosphorus-, arsenic- or antimony-containing ligand of the formula I or II and d, e, f, g are integers which depend on the valence and type of metal and also on the number of coordination sites occupied by the ligand G. e and f preferably each have, independently of one another, a value of at least 1, for example 1, 2 or 3. The sum of e and f is preferably from 2 to 5. If desired, the complexes of the metal Z with the ligands G according to the present invention may further comprise at least one additional ligand which is not according to the present invention, e.g. a ligand selected from the group consisting of triarylphosphines, in particular triphenylphosphine, triarylphosphites, triarylphosphinites, triarylphosphonites, phosphabenzenes, trialkylphosphines and phosphametallocenes. Such complexes of the metal Z with ligands according to and not according to the present invention are formed, for example, in an eqilibrium reaction after addition of a ligand which is not according to the present invention to a complex of the formula H$_g$Z$_d$(CO)$_e$G$_f$.

In a preferred embodiment, the hydroformylation catalysts are prepared in situ in the reactor used for the hydroformylation reaction. However, if desired, the catalysts of the present invention can also be prepared separately and isolated by customary methods. To prepare the catalysts of the present invention in situ, a compound of the formula I or II, a compound or a complex of a metal of transition group VIII, if desired one or more additional ligands which are not according to the present invention and optionally an activating agent can be reacted in an inert solvent under the hydroformylation conditions.

Suitable rhodium compounds or complexes are, for example, rhodium(II) and rhodium(III) salts such as rhodium(III) chloride, rhodium(III) nitrate, rhodium(III) sulfate, potassium rhodium sulfate, rhodium(II) or rhodium(III) carboxylates, rhodium(II) and rhodium(III) acetate, rhodium (III) oxides, salts of rhodic(III) acid, trisammonium hexachlororhodate(III), etc. Rhodium complexes such as dicarbonylrhodium acetylacetonate, acetylacetonatobis(ethylene)rhodium(I), etc., are also suitable. Preference is given to using dicarbonylrhodium acetylacetonate or rhodium acetate.

Ruthenium salts or compounds are likewise suitable. Suitable ruthenium salts are, for example, ruthenium(III) chloride, ruthenium(IV), ruthenium(VI) or ruthenium(VIII) oxide, alkali metal salts of ruthenium oxo acids, e.g. K$_2$RuO$_4$ or KRuO$_4$. Complexes such as RuHCl (CO)(PPh$_3$)$_3$ are also suitable. It is also possible to use metal carbonyls of ruthenium, e.g. dodecacarbonyltriruthenium or octadecacarbonylhexaruthenium, or mixed forms in which CO has been partly replaced by ligands of the formula PR$_3$, e.g. Ru(CO)$_3$(PPh$_3$)$_2$, in the process of the present invention.

Examples of suitable cobalt compounds are cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthenoate, and also the cobalt-caprolactamate complex. Here too, it is possible to use carbonyl complexes of cobalt, e.g. octacarbonyldicobalt, dodecacarbonyltetracobalt and hexadecacarbonylhexacobalt.

The compounds mentioned and further suitable compounds of cobalt, rhodium, ruthenium and iridium are known and are commercially available or their preparation is sufficiently well described in the literature or they can be prepared by a person skilled in the art in a manner analogous to the known compounds.

Suitable activating agents are, for example, Brönsted acids, Lewis acids, e.g. BF$_3$, AlCl$_3$, ZnCl$_2$, and Lewis bases.

As solvents, preference is given to using the aldehydes which are formed in the hydroformylation of the respective olefins, and also their higher-boiling downstream reaction products, e.g. the products of aldol condensation. Further suitable solvents are aromatics such as toluene and xylenes, hydrocarbons or mixtures of hydrocarbons, also for dilution of the abovementioned aldehydes and the downstream products of the aldehydes. Further solvents are esters of aliphatic carboxylic acids with alkanols, for example ethyl acetate or Texanol®, ethers such as tert-butyl methyl ether and tetrahydrofuran. In the case of sufficiently hydrophilic ligands, it is also possible to use alcohols such as methanol, ethanol, n-propanol, isopropanol, n-butanol, isobutanol, ketones such as acetone and methyl ethyl ketone, etc. Furthermore, it is also possible to use "ionic liquids" as solvents. These are liquid salts, for example N,N'-dialkyl-imidazolium salts such as N-butyl-N'-methylimidazolium salts, tetraalkylammonium salts such as tetra-n-butylammonium salts, N-alkylpyridinium salts such as N-butylpyridinium salts, tetraalkylphosphonium salts such as trishexyl(tetradecyl)-phosphonium salts, e.g. the tetrafluoroborates, acetates, tetrachloroaluminates, hexafluorophosphates, chlorides and tosylates.

Furthermore, the reactions can also be carried out in water or aqueous solvent systems comprising water together with a water-miscible solvent, for example an alcohol such as methanol, ethanol, n-propanol, isopropanol, n-butanol, isobutanol, a ketone such as acetone or methyl ethyl ketone or another solvent. For this purpose, use is made of ligands of the formula I or II which have been modified with polar groups, for example ionic groups such as SO$_3$Me, CO$_2$Me where Me=Na, K or NH$_4$ or such as N(CH$_3$)$_3$$^+$. The reactions are then carried out in the form of a two-phase catalysis, with the catalyst being present in the aqueous phase and starting materials and products forming the organic phase. The reaction in the "ionic liquids" can also be carried out as a two-phase catalysis.

The molar ratio of pnicogen chelate compound I or II to the metal of transition group VIII in the hydroformylation medium is generally in the range from about 1:1 to 1000:1, preferably from 1:1 to 100:1, in particular from 1:1 to 50:1.

Substrates suitable for the hydroformylation process of the present invention are in principle all compounds which contain one or more ethylenically unsaturated double bonds. These include, for example, olefins such as α-olefins, internal straight-chain and internal branched olefins. Suitable α-olefins are, for example, propene, 1-butene, 1-pentene, 1-hexene, 1-heptene, 1-octene, 1-nonene, 1-decene, 1-undecene, 1-dodecene, etc.

Preferred branched, internal olefins are $C_4$–$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for hydroformylation are $C_5$–$C_8$-cycloalkenes such as cyclopentene, cyclohexene, cycloheptene, cyclooctene and their derivatives, e.g. their $C_1$–$C_{20}$-alkyl derivatives having from 1 to 5 alkyl substituents. Further olefins suitable for hydroformylation are vinylaromatics such as styrene, α-methylstyrene, 4-isobutylstyrene, etc. Other olefins suitable for hydroformylation are α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$–$C_{20}$-alkenols, $C_1$–$C_{20}$-alkenediols and alkadienols such as 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

The unsaturated compound used for the hydroformylation is preferably selected from among internal linear olefins and olefin mixtures comprising at least one internal linear olefin. Preferred linear (straight-chain) internal olefins are $C_4$–$C_{20}$-olefins such as 2-butene, 2-pentene, 2-hexene, 3-hexene, 2-heptene, 3-heptene, 2-octene, 3-octene, 4-octene, etc., and mixtures thereof.

The hydroformylation process of the present invention is preferably carried out using an industrially available olefin mixture which, in particular, comprises at least one internal linear olefin. Such mixtures include, for example, the Ziegler olefins obtained by targeted ethene oligomerization in the presence of alkylaluminum catalysts. These are essentially unbranched olefins having a terminal double bond and an even number of carbon atoms. Further suitable olefin mixtures of this type are olefins obtained by ethene oligomerization in the presence of various catalyst systems, e.g. the predominantly linear α-olefins obtained in the presence of alkylaluminum chloride/titanium tetrachloride catalysts, and the α-olefins obtained in the presence of nickel-phosphine catalysts in the Shell Higher Olefin Process (SHOP). Further suitable industrially available olefin mixtures are obtained in paraffin dehydrogenation of appropriate petroleum fractions, e.g. kerosene or diesel oil fractions. To convert paraffins, predominantly n-paraffins, into olefins, use is made of essentially three processes:

thermal cracking (steam cracking),
catalytic dehydrogenation and
chemical dehydrogenation by chlorination and dehydrochlorination.

Thermal cracking leads predominantly to α-olefins, while the other variants give olefin mixtures which generally further comprise relatively large proportions of olefins having an internal double bond. Further suitable olefin mixtures are the olefins obtained in metathesis or telomerization reactions. These include, for example, the olefins from the Phillips triolefin process, a modified SHOP comprising ethylene oligomerization, double bond isomerization and subsequent metathesis (ethenolysis).

Further industrial olefin mixtures which are suitable for use in the hydroformylation process of the present invention may be selected from among dibutenes, tributenes, tetrabutenes, dipropenes, tripropenes, tetrapropenes, mixtures of butene isomers, in particular raffinate II, dihexenes, dimers and oligomers from the Dimersol® process of IFP, the Octol process® of Hüls, the Polygas® process, etc.

Preference is given to a process in which the hydroformylation catalyst is prepared in situ by reacting at least one compound of the formula I or II, a compound or a complex of a metal of transition group VIII and, if appropriate, an activating agent in an inert solvent under the hydroformylation conditions.

The hydroformylation reaction can be carried out continuously, semicontinuously or batchwise.

Suitable reactors for a continuous reaction are known to those skilled in the art and are described, for example, in Ullmanns Encyklopädie der technischen Chemie, vol. 1, 3rd edition, 1951, p. 743 ff.

Suitable pressure-rated reactors are likewise known to those skilled in the art and are described, for example, in Ullmanns Encyklopädie der technischen Chemie, vol. 1, 3rd edition, 1951, p. 769 ff. In general, the process of the present invention is carried out using an autoclave which may be provided with a stirrer and an internal liner.

The composition of the synthesis gas comprising carbon monoxide and hydrogen used in the process of the present invention can vary within a wide range. The molar radio of carbon monoxide to hydrogen is generally from about 5:95 to 70:30, preferably from about 40:60 to 60:40. Particular preference is given to using a molar ratio of carbon monoxide to hydrogen in the region of 1:1.

The temperature in the hydroformylation reaction is generally in a range from about 20 to 180° C., preferably from about 50 to 150° C. The reaction is generally carried out at the partial pressure of the reaction gas at the chosen reaction temperature. In general, the pressure is in a range from about 1 to 700 bar, preferably from 1 to 600 bar, in particular from 1 to 300 bar. The reaction pressure can be varied depending on the activity of the novel hydroformylation catalyst used. In general, the catalysts of the present invention based on phosphorus-, arsenic- or antimony-containing compounds allow a reaction at relatively low pressures, e.g. in the range from 1 to 100 bar.

The hydroformylation catalysts used according to the present invention and the hydroformylation catalysts of the present invention can be separated from the reaction mixture after the hydroformylation reaction by methods known to those skilled in the art and can generally be reused for the hydroformylation.

The above-described catalysts of the present invention which comprise chiral compounds of the formula I are suitable for enantioselective hydroformylation.

The above-described catalysts can also be immobilized on a suitable support, e.g. a support made of glass, silica gel, synthetic resins, etc., in a suitable manner, e.g. by bonding via functional groups suitable as anchor groups, adsorption, grafting, etc. They are then also suitable for use as solid-state catalysts.

Surprisingly, the catalysts prepared from the novel pnicogen chelate compounds of the formula I or II not only have a high activity in respect of the hydroformylation of terminal olefins but likewise have a high activity in respect of the isomerizing hydroformylation of olefins having internal double bonds to form aldehyde products having a high linearity. Advantageously, hydrogenation of the olefins takes place to only a very slight extent under hydroformylation conditions when using the catalysts of the present invention.

Surprisingly, catalysts based on pnicogen chelate compounds of the formula II have a particularly high stability under the hydroformylation conditions, so that they generally make it possible to achieve longer catalyst operating lives than do prior art catalysts based on conventional monodentate and polydentate ligands. Thus, we have found that pyrrole-phosphorus compounds of the prior art in which one or more unsubstituted pyrrole groups are bound via their nitrogen atom to the phosphorus atom tend to decompose or to form undesirable reaction products. Appreciable decomposition is thus induced even by visible light and/or temperatures in the vicinity of room temperature and cannot be prevented even by use of a protective gas when using monodentate ligands based on unsubstituted pyrrole groups, for example trispyrrolylphosphine, and also when using chelating ligands having bridging groups different from those in the ligands of the present invention, for example the ligands described in U.S. Pat. No. 5,710,344. Appreciable formation of polymeric impurities can occur in the presence of aldehydes. When using such pyrrole-phosphorus compounds as ligands for hydroformylation catalysts, there is thus a loss of catalyst and desired product which, particularly in the case of multistage processes comprising such a hydroformylation step (e.g. the preparation of 2-propylheptanol), has an adverse effect on the economics. It has now surprisingly been found that use of pnicogen compounds, in particular phosphorus compounds, of the formula II in which a substituted pyrrole group and/or a pyrrole group integrated into a fused ring system is bound covalently via its pyrrole nitrogen to the phosphorus atom substantially suppresses the formation of undesirable products.

The present invention further provides a process for preparing 2-propylheptanol, which comprises
a) hydroformylating butene or a butene-containing $C_4$-hydrocarbon mixture by means of carbon monoxide and hydrogen in the presence of a hydroformylation catalyst to give an n-valeraldehyde-containing hydroformylation product, where the hydroformylation catalyst comprises at least one complex of a metal of transition group VIII with at least one ligand of the formula I or II as defined above,
b) if desired, subjecting the hydroformylation product to a fractionation to give an n-valeraldehyde-enriched fraction,
c) subjecting the hydroformylation product obtained in step a) or the n-valeraldehyde-enriched fraction obtained in step b) to an aldol condensation,
d) catalytically hydrogenating the products of the aldol condensation by means of hydrogen to form alcohols, and
e) if desired, subjecting the hydrogenation products to a fractionation to give a 2-propylheptanol-enriched fraction.

In step a), preference is given to using a hydroformylation catalyst comprising at least one complex of a metal of transition group VIII with at least one ligand of the formula II. As regards suitable and preferred ligands of the formula II, that which has been said above is hereby incorporated by reference at this point.

a) Hydroformylation

As starting material for the hydroformylation, it is possible to use either virtually pure 1-butene or mixtures of 1-butene with 2-butene and industrially available $C_4$-hydrocarbon streams comprising 1-butene and/or 2-butene. Preference is given to $C_4$ fractions which are available in large quantities from FCC plants and from steam crackers. These consist essentially of a mixture of the isomeric butenes and butane.

$C_4$-hydrocarbon streams suitable as starting material comprise, for example, from 50 to 99 mol %, preferably from 60 to 90 mol %, of butenes and from 1 to 50 mol %, preferably from 10 to 40 mol %, of butanes. The butene fraction preferably comprises from 40 to 60 mol % of 1-butene, from 20 to 30 mol % of 2-butene and less than 5 mol %, in particular less than 3 mol %, of isobutene (based on the butene fraction). A particularly preferred feedstock is raffinate II, which is an isobutene-depleted $C_4$ fraction from an FCC plant or a steam cracker.

Hydroformylation catalysts based on the pnicogen chelate compounds used as ligands according to the present invention advantageously have a high n-selectivity even when using 2-butene and 2-butene-containing hydrocarbon mixtures as starting material. Thus, such feedstocks can be used economically in the process of the present invention, since the desired n-valeraldehyde is obtained in good yields.

As regards suitable and preferred hydroformylation catalysts, activators, solvents, reaction conditions and reactors for the hydroformylation in step a), or that which has been said above in respect of hydroformylation is hereby incorporated by reference at this point.

The hydroformylation catalysts of the present invention can be separated from the product mixture from the hydroformylation reaction by customary methods known to those skilled in the art and can generally be reused for the hydroformylation.

b) Fractionation

In a useful process variant, the product-enriched fraction obtained from step a) is, after the catalyst system has been separated off, subjected to a further fractionation to give an n-valeraldehyde-enriched fraction. The fractionation of the hydroformylation product to give an n-valeraldehyde-enriched fraction and an n-valeraldehyde-depleted fraction is carried out by customary methods known to those skilled in the art. Preference is given to distillation using known separation apparatuses such as distillation columns, e.g. tray columns which may, if desired, be provided with bubble caps, sieve plates, sieve trays, valves, etc., evaporators such as thin film evaporators, falling film evaporators, wiped film evaporators, etc.

c) Aldol Condensation

Two molecules of $C_5$-aldehyde can be condensed to form $\alpha,\beta$-unsaturated $C_{10}$-aldehydes. The aldol condensation is carried out in a manner known per se, e.g. in the presence of an aqueous base such as sodium hydroxide or potassium hydroxide. As an alternative, it is also possible to use a heterogeneous basic catalyst such as magnesium oxide and/or aluminum oxide (cf., for example, EP-A 792 862). This results in the condensation of two molecules of n-valeraldehyde to form 2-propyl-2-heptenal. If the hydroformylation product obtained in step a) or after the fractionation in step b) further comprises other $C_5$-aldehydes such as 2-methylbutanal and possibly 2,2-dimethylpropanal and 3-methylbutanal respectively, these likewise undergo an aldol condensation, resulting in condensation products of all possible aldehyde combinations, for example, 2-propyl-4-methyl-2-hexenal. The presence of a proportion of these condensation products, e.g. up to 30% by weight, does not stand in the way of advantageous further processing to 2-propylheptanol-containing $C_{10}$-alcohol mixtures suitable as plasticizer alcohols.

d) Hydrogenation

The products of the aldol condensation can be catalytically hydrogenated by means of hydrogen to form $C_{10}$-alcohols, in particular 2-propylheptanol.

The hydrogenation of the $C_{10}$-aldehydes to the $C_{10}$-alcohols can in principle be carried out using the same catalysts as in the hydroformylation, usually at higher temperature; however, preference is given to more selective hydrogenation catalysts which are used in a separated hydrogenation step. Suitable hydrogenation catalysts are generally transition metals such as Cr, Mo, W, Fe, Rh, Co, Ni, Pd, Pt, Ru, etc., or mixtures thereof, which can be applied to supports such as activated carbon, aluminum oxide, kieselguhr, etc., to increase the activity and stability. To increase the catalytic activity, Fe, Co and preferably Ni can also be used in the form of Raney catalysts, viz. as metal sponge having a very high surface area. Depending on the activity of the catalyst, the hydrogenation of the $C_{10}$-aldehydes is preferably carried out at elevated temperatures and superatmospheric pressure. The hydrogenation temperature is preferably from about 80 to 250° C., and the pressure is preferably from about 50 to 350 bar.

The crude hydrogenation product can be worked up by customary methods, e.g. by distillation, to give the $C_{10}$-alcohols.

e) Fractionation

If desired, the hydrogenation products can be subjected to a further fractionation to give a 2-propylheptanol-enriched fraction and a 2-propylheptanol-depleted fraction. This fractionation can be carried out by customary methods known to those skilled in the art, e.g. by distillation.

Hydroformylation catalysts comprising a complex of at least one metal of transition group VIII of the Periodic Table with, as ligand, at least one pnicogen chelate compound of the formula I and in particular a pyrrole-phosphorus compound of the formula II having a substituted and/or fused pyrrole skeleton can advantageously be used in a process for preparing 2-propylheptanol. The catalysts display a high n-selectivity in such a process, so that a good yield of n-valeraldehyde is obtained both when using virtually pure 1-butene and when using 1-butene/2-butene-containing hydrocarbon mixtures, for example, $C_4$ fractions. The catalysts used according to the present invention are also suitable for double bond isomerization from an internal position to a terminal position, so that n-valeraldehyde is obtained in good yields even when using 2-butene and hydrocarbon mixtures having relatively high concentrations of 2-butene. The catalysts based on substituted or fused pyrrole skeletons which are used according to the present invention advantageously undergo virtually no decomposition under the hydroformylation conditions, i.e. in the presence of aldehydes. A further advantage is that virtually no decomposition products are formed in the presence of atmospheric oxygen and/or light and/or acids and/or at room temperature and elevated temperatures, e.g. up to about 150° C., so that it is not necessary to use complicated measures for stabilizing the hydroformylation catalyst used, particularly during work-up.

The invention further provides for the use of catalysts comprising at least one complex of a metal of transition group VIII with at least one compound of the formula I or II, as described above, for hydroformylation, hydrocyanation, carbonylation and hydrogenation.

As mentioned, hydrocyanation of olefins is a further application area for the catalysts of the present invention. The hydrocyanation catalysts of the present invention also comprise complexes of a metal of transition group VIII, in particular cobalt, nickel, ruthenium, rhodium, palladium, platinum, preferably nickel, palladium or platinum and very particularly preferably nickel. In general, the metal is present in zero-valent form in the metal complex according to the present invention. The preparation of the metal complexes can be carried out as described above for the use as hydroformylation catalysts. The same applies to the in-situ preparation of the hydrocyanation catalysts of the present invention.

A nickel complex suitable for preparing a hydrocyanation catalyst is, for example, bis(1,5-cyclooctadiene)nickel (0).

If desired, the hydrocyanation catalysts can be prepared in situ by a method analogous to the process described for the hydroformylation catalysts.

The invention therefore further provides a process for preparing nitriles by catalytic hydrocyanation, in which the hydrocyanation is carried out in the presence of at least one of the novel catalysts described above. Olefins suitable for hydrocyanation are generally the same as the olefins mentioned above as starting materials for hydroformylation. A specific embodiment of the process of the present invention comprises the preparation of mixtures of monoolefinic $C_5$-mononitriles having nonconjugated C=C and C≡N bonds by catalytic hydrocyanation of 1,3-butadiene or 1,3-butadiene-containing hydrocarbon mixtures and the isomerization/further reaction of these in the presence of at least one catalyst according to the present invention to form saturated $C_4$-dinitriles, preferably adiponitrile. When hydrocarbon mixtures are used for preparing monoolefinic $C_5$-mononitriles by the process of the present invention, preference is given to using a hydrocarbon mixture having a 1,3-butadiene content of at least 10% by volume, preferably at least 25% by volume, in particular at least 40% by volume.

1,3-Butadiene-containing hydrocarbon mixtures are obtainable on an industrial scale. Thus, for example, the processing of petroleum by steam cracking of naphtha gives a hydrocarbon mixture known as $C_4$ fraction which has a high total olefin content. About 40% of this mixture is 1,3-butadiene and the remainder is made up of monoolefins and multiply unsaturated hydrocarbons and alkanes. These streams always contain small proportions of generally up to 5% of alkynes, 1,2-dienes and vinylacetylene.

Pure 1,3-butadiene can be isolated from industrially available hydrocarbon mixtures by, for example, extractive distillation.

The catalysts of the present invention can advantageously be used for the hydrocyanation of such olefin-containing, in particular 1,3-butadiene-containing, hydrocarbon mixtures, generally also without prior purification of the hydrocarbon mixture by distillation. If present, olefins which adversely affect the catalysts, e.g. alkynes or cumulenes, may be removed from the hydrocarbon mixture by selective hydrogenation prior to the hydrocyanation. Suitable methods of carrying out selective hydrogenation are known to those skilled in the art.

The hydrocyanation according to the present invention can be carried out continuously, semicontinuously or batchwise. Suitable reactors for a continuous reaction are known to those skilled in the art and are described, for example, in Ullmanns Enzyklopädie der technischen Chemie, volume 1, 3rd edition, 1951, p. 743 ff. Preference is given to using a cascade of stirred vessels or a tube reactor for the continuous variant of the process of the present invention. Suitable reactors, which may be pressure-rated, for the semicontinuous or continuous embodiments are known to those skilled in the art and are described, for example, in Ullmanns Enzyklopädie der technischen Chemie, volume 1, 3rd edition, 1951, p. 769 ff. In general, the process of the present invention is carried out in an autoclave which may, if desired, be provided with a stirrer and an internal liner.

The hydrocyanation catalysts of the present invention can be separated from the reaction mixture after the hydrocyanation reaction by customary methods known to those skilled in the art and can generally be reused for the hydrocyanation.

The invention further provides a process for the carbonylation of compounds containing at least one ethylenically unsaturated double bond by reaction with carbon monoxide and at least one compound containing a nucleophilic group in the presence of a carbonylation catalyst based on a pnicogen chelate ligand of the formula I or II.

The novel carbonylation catalysts, too, encompass complexes of a metal of transition group VIII, preferably nickel, cobalt, iron, ruthenium, rhodium or palladium, in particular palladium. The preparation of the metal complexes can be carried out as described above for the hydroformylation catalysts and hydrocyanation catalysts. The same applies to the in-situ preparation of the carbonylation catalysts of the present invention.

Suitable olefins for the carbonylation are the olefins mentioned above in general terms as starting materials for hydroformylation and hydrocyanation.

The compounds containing a nucleophilic group are preferably selected from among water, alcohols, thiols, carboxylic esters, primary and secondary amines.

A preferred carbonylation reaction is the conversion of olefins into carboxylic acids by reaction with carbon monoxide and water (hydrocarboxylation). This includes, in particular, the reaction of ethylene with carbon monoxide and water to form propionic acid.

The invention further provides for the use of catalysts comprising a P-, As- or Sb-containing compound according to the present invention, as described above, for hydroformylation, hydrocyanation, carbonylation, hydrogenation, olefin oligomerization and olefin polymerization and for metathesis.

The invention is illustrated by the following, nonrestrictive examples.

EXAMPLES

The following ligands were used:

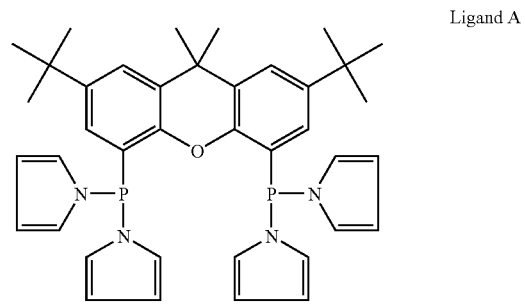

Ligand A

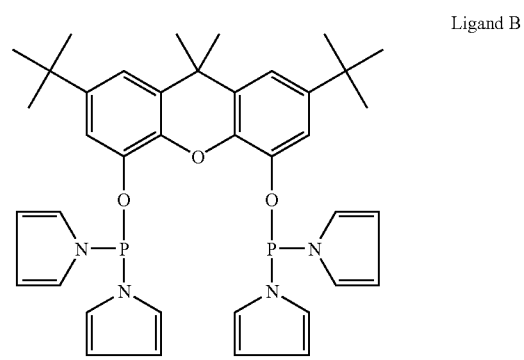

Ligand B

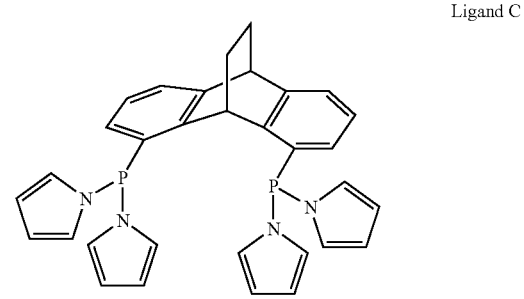

Ligand C

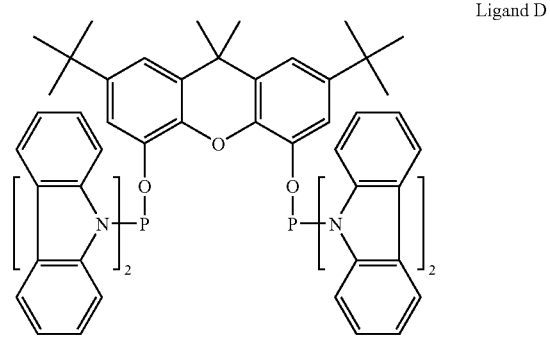

Ligand D

Ligand E
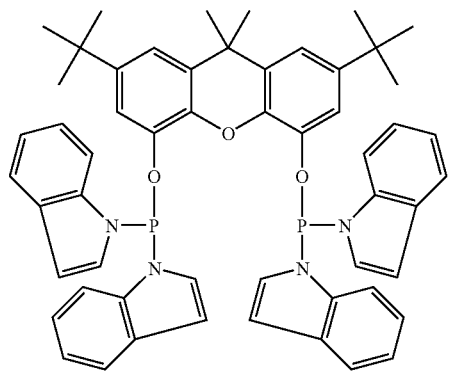
Ligand F
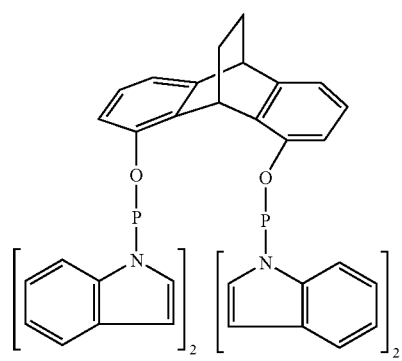
Ligand G
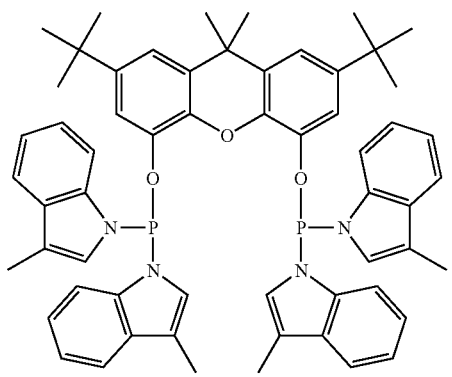
Ligand H
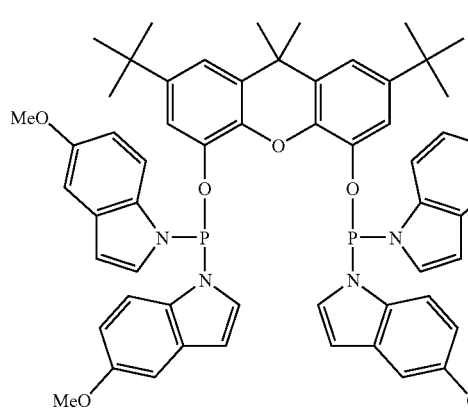
Ligand I
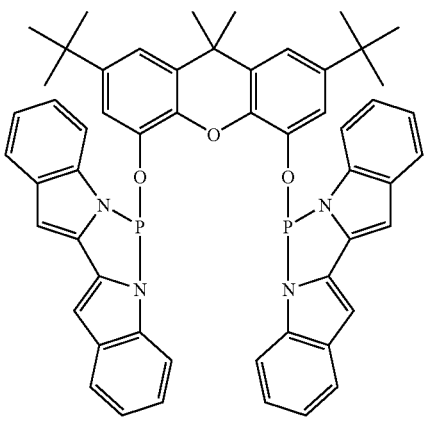
Ligand K
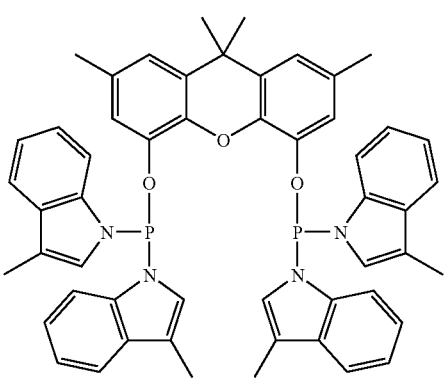
Ligand L
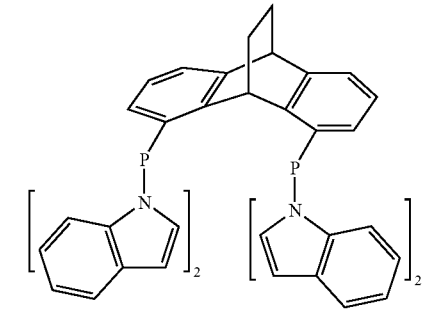
Comparative ligand CLA
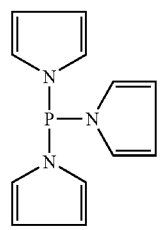
Comparative ligand CLB
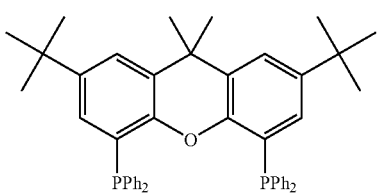

Comparative ligand LC

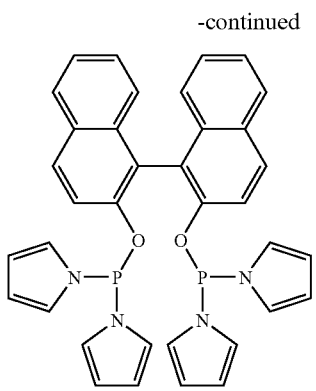

Example 1

Synthesis of Ligand A 5.2 g (38 mmol) of PCl$_3$ and 5.1 g (76 mmol) of pyrrole together with 200 ml of dried tetrahydrofuran (THF) were placed in a reaction vessel under argon at −65° C. 11.5 g (115 mmol) of triethylamine were added to this mixture and the reaction mixture was stirred overnight at room temperature. The resulting precipitate was filtered off from the liquid reaction mixture under reduced pressure and excess THF and triethylamine were distilled off at 60° C. The residue was taken up in 50 ml of toluene and residual precipitated triethylamine hydrochloride was filtered off from this solution. The solution obtained was stored until needed for further processing.

5 g (13.3 mmol) of 1,8-dibromo-3,6-di-tert-butylxanthene together with 150 ml of dried THF were placed in a reaction vessel at −50° C. under argon. 12.3 ml (30.6 mmol) of a 2.5 molar solution of n-butyllithium in hexane were added dropwise and, after the addition was complete, stirred for another 2 hours at −50° C., resulting in formation of a precipitate. This solution was subsequently added at −70° C. to the previously prepared toluene solution. The temperature of the exothermic reaction was kept below −50° C. by cooling. After stirring for 1 hour, the reaction mixture was evaporated under reduced pressure, the residue was taken up in dichloromethane, then evaporated again, hexane was added and the mixture was stirred. The solid formed was recrystallized twice from hot methanol. Pure ligand A was obtained in a yield of 1.1 g (13% of theory).

Example 2

Synthesis of Ligand B 5 g (13.3 mmol) of 1,8-dibromo-3,6-di-tert-butylxanthene together with THF were placed in a reaction vessel under argon. At −50° C., 12.3 ml (30.7 mmol) of a 2.5 molar n-butyllithium solution in hexane were added. The reaction mixture was stirred for 2 hours, resulting in formation of a colorless suspension. At 0° C., 100 ml (100 mmol) of a 1 molar solution of BH$_3$ in THF were added dropwise and the mixture was stirred overnight at 5–15° C. It was subsequently carefully hydrolyzed at 0° C. using 25 ml of water. 3 N KOH (7.4 g of KOH in 32 g of H$_2$O) and 10.4 g of 30% strength H$_2$O$_2$ solution were carefully added to the reaction mixture and the resulting mixture was refluxed for 2 hours. After cooling to room temperature, it was neutralized using 18% strength hydrochloric acid. After phase separation, the organic phase was washed twice with NaCl solution, dried over Na$_2$SO$_4$ and evaporated to dryness. 1,8-Dihydroxy-3,6-di-tert-butylxanthene was obtained in a yield of 4.7 g (100% of theory).

5.2 g (38 mmol) of PCl$_3$ and 5.1 g (76 mmol) of pyrrole together with THF were placed in a reaction vessel at −65° C. under argon. 1.5 g (114 mmol) of triethylamine were subsequently added slowly and the mixture was stirred at room temperature for 48 hours. 4.7 g (13.3 mmol) of 1,8-dihydroxy-3,6-di-tert-butylxanthene in 50 ml of THF were added thereto at room temperature, resulting in the temperature rising to 30° C. After stirring overnight, the solid formed was filtered off under reduced pressure, washed with THF and the combined organic phases were evaporated, giving a brown oil. The oil was recrystallized three times from hexane. Ligand B was obtained in a yield of 1.1 g (12% of theory).

Example 3 (Comparative Example)

Synthesis of Ligand CLA (Comparative Ligand) and Storage at Room Temperature

Comparative ligand CLA was prepared as described by K. G. Moloy et al., J. Am. Chem. Soc. 117, pp. 7696–7710 (1995). The synthesis leads to a clean product having a $^{31}$P-NMR chemical shift of +79 ppm (C$_6$D$_6$). After storage of the compound under argon for five days at room temperature, an appreciable dark coloration was observed. After eight weeks, a tar-like compound which could no longer be used as catalyst was formed.

Example 4

Synthesis of Ligand C

Using the method of Maverick et al. (Inorg. Chem. 36, 5826 (1997)), 66.7 g (240 mmol) of 1,8-dichloroanthraquinone, 113.3 g (1.12 mol) of KBr, 3.3 g (50 mmol) of CuCl$_2$ and 113.4 ml of 85% strength phosphoric acid were suspended in 500 ml of nitrobenzene and the water was distilled off at 200° C. The mixture was subsequently refluxed for 72 hours. After cooling, the solid product was taken up in methanol and dichloromethane, evaporated to dryness and washed with acetone. An 8:1 mixture of 1,8-dibromoanthraquinone/1-bromo-8-chloroanthraquinone was obtained in a yield of 46 g (60% of theory).

23.6 g (65 mmol) of 1,8-dibromoanthraquinone were suspended in 250 ml of methanol. At 10° C., 9.9 g (260 mmol) of NaBH$_4$ were added slowly and the mixture was subsequently stirred at 0° C. for 2 hours. The mixture was poured onto 800 ml of ice, stirred and filtered under reduced pressure. The solid was subsequently suspended in 400 ml of 18% strength hydrochloric acid and stirred at 70° C. for 5 hours, after which it was once again filtered off under reduced pressure, washed until neutral and dried. The solid was stirred with 14.8 g of NaBH$_4$ in 250 ml of isopropanol at 85° C. (reflux) for 3 hours, brought to a pH of 7 by addition of dilute hydrochloric acid, filtered off with suction and washed with water. 1,8-Dibromoanthracene was obtained in a yield of 16.2 g (74% of theory).

100 g (298 mmol) of 1,8-dibromoanthracene and 0.63 g (4 mmol) of p-tert-butylcatechol were dissolved in 800 g of toluene and treated with 45 bar of ethene in an autoclave for 5 minutes. The mixture was subsequently stirred at 150° C. for 3 days. The reaction mixture was extracted with 10% strength aqueous sodium hydroxide and washed with distilled water. The organic phase was separated off and evaporated. The residue was recrystallized twice from methanol. 1,8-Dibromomethanoanthracene was obtained in a yield of 60 g (55% of theory).

5.2 g (38 mmol) of $PCl_3$ and 5.1 g (76 mmol) of pyrrole together with dry tetrahydrofuran were placed in a reaction vessel at $-78°$ C. under argon. 11.5 g (114 mmol) of triethylamine were added and the mixture was stirred overnight at room temperature. The resulting precipitate was filtered off and excess tetrahydrofuran and triethylamine were distilled off. The residue was taken up in toluene and filtered. The solution was stored.

4.8 g (13.3 mmol) of 1,8-dibromomethanoanthracene together with 150 ml of dry tetrahydrofuran were placed in a reaction vessel at $-50°$ C., and 12.3 ml of a 2.5 molar n-butyllithium solution in hexane (30.6 mmol) were subsequently added and the mixture was stirred at $-50°$ C. for 2 hours. At $-70°$ C., this mixture was added to the previously prepared solution of bispyrrolylphosphorus chloride in toluene, resulting in the temperature rising to $-50°$ C. After stirring for 1 hour, the mixture was evaporated and the solid was taken up in dichloromethane, the mixture was filtered, the filtrate was evaporated and the residue was stirred with hexane. The product was recrystallized from hot methanol. Ligand C was obtained in a yield of 1.6 g (23% of theory).

Example 5

Hydroformylation of a Butene/butane Mixture Using Ligand A 3.0 mg of $Rh(CO)_2acac$ and 75 mg of ligand A (57 ppm of Rh, ligand/rhodium ratio=10/1) were weighed out separately, each dissolved in 5 g of toluene, mixed and treated at 120° C. with 10 bar of synthesis gas ($CO:H_2$=1:1). After 30 minutes, the mixture was depressurized, 11 g of butene/butane mixture (45% of 1-butene, 40% of 2-butene, 15% of butanes) were then injected and a reaction pressure of 20 bar was set at 120° C. by means of $CO/H_2$ (1:1). After 4 hours, the autoclave was vented via a cold trap and both reaction products (reactor and cold trap) were analyzed by means of gas chromatography. The conversion of butenes was 47%, the aldehyde selectivity was 96% and the linearity was 95%. (Linearity: ratio of n-aldehyde to all aldehydes formed×100)

Example 6

Hydroformylation of a Butene/butane Mixture Using Ligand B 3.0 mg of $Rh(CO)_2acac$ and 79 mg of ligand B (57 ppm of Rh, ligand/rhodium=10/1) were weighed out separately, each dissolved in 5 g of toluene, mixed and treated at 120° C. with 10 bar of synthesis gas ($CO:H_2$=1:1). After 30 minutes, the mixture was depressurized, 11 g of butene/butane mixture (45% of 1-butene, 40% of 2-butene, 15% of butanes) were then injected and the mixture was hydroformylated at 120° C. and 20 bar for 4 hours. The conversion of butenes was 58%, the aldehyde selectivity was 97% and the linearity was 94%.

Example 7

Hydroformylation of a Butene/butane Mixture Using Ligand B 6.0 mg of $Rh(CO)_2acac$ and 161 mg of ligand B (112 ppm of Rh, ligand/rhodium=10/1) were weighed out separately, each dissolved in 7.5 g of toluene, mixed and treated at 100° C. with 10 bar of synthesis gas ($CO:H_2$=1:2). After 30 minutes, the mixture was depressurized, 6.2 g of butene/butane mixture (45% of 1-butene, 40% of 2-butene, 15% of butanes) were then injected and the mixture was hydroformylated at 100° C. and 22 bar for 4 hours. The conversion of butenes was 85%, the aldehyde selectivity was 89% and the linearity was 99%.

Example 8

Hydroformylation of 2-butene Using Ligand B 3.6 mg of $Rh(CO)_2acac$ and 162 mg of ligand B (116 ppm of Rh, ligand/rhodium=10/1) were weighed out separately, each dissolved in 7.5 g of toluene, mixed and treated at 100° C. with 10 bar of synthesis gas ($CO:H_2$=1:2). After 30 minutes, the mixture was depressurized, 5.5 g of 2-butene were then injected and the mixture was hydroformylated at 100° C. and 22 bar for 4 hours. The conversion of 2-butene was 79%, the aldehyde selectivity was 92% and the linearity was 95%.

Example 9

Hydroformylation of 1-octene Using Ligand B 0.8 mg of $Rh(CO)_2acac$ and 20.7 mg of ligand B (60 ppm of Rh, ligand/rhodium=11/1) were weighed out separately, each dissolved in 1.3 g of toluene, mixed and treated at 100° C. with 10 bar of synthesis gas ($CO:H_2$=1:1). After 30 minutes, the mixture was depressurized, 2.5 g of 1-octene were then injected and the mixture was hydroformylated at 100° C. and 10 bar for 4 hours. The conversion was 98%, the aldehyde selectivity was 83% and the linearity was 98%. The proportion of $\alpha$-isomers (n-nonanal+isononanal) was 100%.

Example 10 (Comparative Example)

Hydroformylation of 1-octene Using Comparative Ligand CLA 0.9 mg of $Rh(CO)_2acac$ and 8 mg of comparative ligand CLA (60 ppm of Rh, ligand/rhodium=10/1) were weighed out separately, each dissolved in 1.5 g of xylene, mixed and treated at 100° C. with 10 bar of synthesis gas ($CO:H_2$=1:1). After 30 minutes, the mixture was depressurized, 3.0 g of 1-octene were then injected and the mixture was hydroformylated at 80° C. and 10 bar for 4 hours. The conversion was 79%, the aldehyde selectivity was 81% and the linearity was 83%. The proportion of $\alpha$-isomers (n-nonanal+isononanal) was 99%.

Example 11

Hydroformylation of 1-octene Using Ligand C 0.9 mg of $Rh(CO)_2acac$ and 18.5 mg of ligand C (60 ppm of Rh, ligand/rhodium=10/1) were weighed out separately, each dissolved in 1.5 g of diphenyl ether, mixed and treated at 100° C. with 10 bar of synthesis gas ($CO:H_2$=1:1). After 60 minutes, the mixture was depressurized, 3.0 g of 1-octene were then injected and the mixture was hydroformylated at 100°°C. and 10 bar for 4 hours. The linearity was 98% and the proportion of $\alpha$-isomers (n-nonanal+isononanal) was 100%.

Example 12

Hydroformylation of 2-octene Using Ligand C 6 mg of Rh(CO)$_2$acac and 124 mg of ligand C (119 ppm of Rh, ligand/rhodium=10/1) were weighed out separately, each dissolved in 5 g of toluene, mixed and treated at 100° C. with 10 bar of synthesis gas (CO:H$_2$=1:2). After 30 minutes, the mixture was depressurized, 10 g of 2-octene were then injected and the mixture was hydroformylated at 100° C. and 10 bar for 4 hours. The linearity was 99% and the proportion of α-isomers (n-nonanal+isononanal) was 100%.

Example 13 (Comparative Example)

Hydroformylation of 2-octene Using Comparative Ligand CLA 0.9 mg of Rh(CO)$_2$acac and 8 mg of comparative ligand CLA (60 ppm of Rh, ligand/rhodium=10/1) were weighed out separately, each dissolved in 1.5 g of xylene, mixed and treated at 100° C. with 10 bar of synthesis gas (CO:H$_2$=1:1). After 30 minutes, the mixture was depressurized, 3.0 g of 2-octene were then injected and the mixture was hydroformylated at 100° C. and 10 bar for 4 hours. The conversion was 74%, the aldehyde selectivity was 44% and the linearity was 51%. The proportion of α-isomers (n-nonanal+isononanal) was 85%.

Example 14 (Comparative Example)

Hydroformylation of a Butene/butane Mixture Using Comparative Ligand CLB 6 mg of Rh(CO)$_2$acac and 96.5 mg of comparative ligand CLB (102 ppm of Rh, ligand/rhodium=6/1) were weighed out separately, each dissolved in 5 g of xylene, mixed and treated at 110° C. with 20 bar of synthesis gas (CO:H$_2$=1:1). After 30 minutes, the mixture was depressurized, 13.4 g of butene/butane mixture (45% of 1-butene, 40% of 2-butene, 15% of butanes) were then added and the mixture was hydroformylated at 110° C. and 20 bar for 3.5 hours. The conversion of butenes was 50%, the aldehyde selectivity was 100% and the linearity was 95%. The unreacted olefin consisted exclusively of 2-butene, i.e. only the 1-butene in the mixture was reacted.

Comparative ligand CLB was prepared as described in Angew. Chem. 111, 349 (1999).

Example 15 (Synthesis of Ligand D)

5.2 g (38 mmol) of PCl$_3$ and 12.7 g (76 mmol) of carbazole together with 200 ml of dried tetrahydrofuran (THF) were placed in a reaction vessel at −65° C. under argon. 11.5 g (115 mmol) of triethylamine were added to this mixture and the reaction mixture was stirred overnight at room temperature. The precipitate formed was filtered off from the liquid reaction mixture under reduced pressure and excess THF and triethylamine were distilled off, going over at a temperature of 60° C. The residue was taken up in 50 ml of toluene and remaining triethylamine hydrochloride which precipitated was filtered off. The solution obtained was stored until it was processed further.

5 g (13.3 mmol) of 1,8-dibromo-3,6-di-tert-butylxanthene together with 150 ml of dried THF were placed in a reaction vessel at −50° C. under argon. 12.3 ml (30.6 mmol) of a 2.5 molar solution of n-butyllithium in hexane were added dropwise and, after the addition was complete, the mixture was stirred at −50° C. for another 2 hours, resulting in formation of a precipitate. This solution was subsequently added at −70° C. to the previously prepared toluene solution. The temperature of the exothermic reaction was kept below −50° C. by cooling. After stirring for 1 hour, the reaction mixture was evaporated under reduced pressure, the residue was taken up in dichloromethane, evaporated again and stirred after addition of hexane. The resulting solid was recrystallized twice from hot methanol. Pure ligand D, which displayed a singlet at +125 ppm in the $^{31}$P-NMR (CDCl$_3$).

Example 16 (Comparative Example)

Storage of Comparative Ligand CLC at Room Temperature

Comparative ligand CLC was prepared as described in U.S. Pat. No. 5,710,344. The synthesis leads to a clean product having a $^{31}$P-NMR chemical shift of +69 ppm (C$_6$D$_6$). After storage of the compound under argon for 10 days at room temperature, an appreciable dark coloration was observed. Examination by $^{31}$P-NMR showed a ligand degradation of 20%.

Example 17 (Comparative Example)

Hydroformylation of 1-octene before Storage at Room Temperature 1.6 mg of Rh(CO)$_2$acac (dicarbonylrhodium acetylacetonate) and 36.9 mg of comparative ligand CLC (106 ppm of Rh, ligand:metal=10/1) were weighed out separately, each dissolved in 1.5 g of Palatinol-AH® (phthalic ester of 2-ethylhexanol from BASF Aktienges.), mixed and treated at 100° C. with 10 bar of synthesis gas (CO:H$_2$=1:1) in a 100 ml autoclave. After 30 minutes, the mixture was depressurized, 3 g of 1-octene were then added and the mixture was hydroformylated at 100° C. and 10 bar for 4 hours. The conversion was 98%, the aldehyde selectivity was 59% and the linearity was 99%. The selectivity to internal octenes was 41%.

Example 18 (Comparative Example)

Hydroformylation of 1-octene after Storage at Room Temperature 1.6 mg of Rh(CO)$_2$acac and 36.9 mg of comparative ligand CLC (106 ppm of Rh, ligand:metal=10/1) were weighed out separately, each dissolved in 1.5 g of Palatinol-AH®, mixed and treated at 100° C. with 10 bar of synthesis gas (CO:H$_2$=1:1). After 30 minutes, the mixture was depressurized, 3 g of 1-octene were then added by means of a syringe and the mixture was hydroformylated at 100° C. and 10 bar for 4 hours. The conversion was 20%, the aldehyde selectivity was 5% and the linearity was 71%. The selectivity to internal octenes was 95%.

Example 19

Hydroformylation of 2-butene Using Ligand D 6.0 mg of Rh(CO)$_2$acac and 238 mg of ligand D (117 ppm of Rh, ligand:metal=9/1) were weighed out separately, each dissolved in 7.5 g of toluene, mixed and treated at 100° C. with 10 bar of synthesis gas (CO:H$_2$=1:2). After 30 minutes, the mixture was depressurized, 5.3 g of 2-butene were then injected and the mixture was hydroformylated at 100° C. and 22 bar for 4 hours. The conversion was 25%, the aldehyde selectivity was 92% and the linearity was 45%.

Examination of the reaction product mixture by $^{31}$P-NMR showed no degradation products of the ligand. The reaction product mixture was a yellow homogeneous solution. After hydroformylation with ligand B a red precipitate was observed which was not the case with unsubstituted pyrrols.

Example 20

Experiments on the Stability of Ligand D

Ligand D was dissolved in $CH_2Cl_2$ and washed with warm water in the presence of air. No color change was observed. Examination by $^{31}$P-NMR showed no degradation products. The ligand was subsequently stored at room temperature without protection from light for four weeks. Here too, no color change was observed. Examination by $^{31}$P-NMR showed no degradation products.

Example 21

Hydroformylation of 3-hexene Using Ligand E 5.4 mg of $Rh(CO)_2$acac and 174 mg of ligand E (107 ppm of Rh, ligand:metal=9/1) were weighed out separately, each dissolved in 7.5 g of toluene, mixed and treated at 100° C. with 10 bar of synthesis gas ($CO:H_2$=1:2). After 30 minutes, the mixture was depressurized, 5 g of 3-hexene were then injected and the mixture was hydroformylated at 120° C. and 12 bar ($CO:H_2$=1:1) for 4 hours. The conversion was 58%, the aldehyde selectivity was 87% and the linearity was 98%.

Example 22

Hydroformylation of 1-octene Using Ligand E 5.1 mg of $Rh(CO)_2$acac and 342 mg of ligand E (100 ppm of Rh, ligand:metal=20/1) were weighed out separately, each dissolved in 5 g of Palatinol-AH®, mixed and treated at 100° C. with 10 bar of synthesis gas ($CO:H_2$=1:2). After 60 minutes, the mixture was depressurized, 10 g of 1-octene were then injected and the mixture was hydroformylated at 120° C. and 20 bar ($CO:H_2$=1:1) for 2 hours. The conversion was 100%, the aldehyde selectivity was 79% and the linearity was 95%.

Example 23

Hydroformylation of a Butene/butane Mixture Using Ligand E 5.0 mg of $Rh(CO)_2$acac and 170 mg of ligand E (94 ppm of Rh, ligand:metal=10/1) were weighed out separately, each dissolved in 6 g of toluene, mixed and treated at 120° C. with 10 bar of synthesis gas ($CO:H_2$=1:2). After 30 minutes, the mixture was depressurized, 9 g of butene/butane mixture (45% of 1-butene, 40% of 2-butene, 15% of butanes) were then injected and the mixture was hydroformylated at 120° C. and 17 bar ($CO:H_2$=1:1) for 4 hours. The conversion of butenes was 91%, the aldehyde selectivity was 100% and the linearity was 91%.

Examination of the reaction product mixture by $^{31}$P-NMR showed no degradation products of the ligand. The reaction product mixture was a yellow homogeneous solution. A red precipitate was not observed. The experiment was repeated in the same autoclave and gave the same result.

Example 24

Experiments on the Stability of Ligand E

Ligand E was dissolved in $CH_2Cl_2$ and washed with warm water in the presence of air. No color change was observed. Examination by $^{31}$P-NMR showed no degradation products. The ligand was subsequently stored at room temperature without protection from light for four weeks. Here too, no color change was observed. Examination by $^{31}$P-NMR showed no degradation products.

Example 25

Reaction of Ligand E with Acids

In a nitrogen-filled glove box, ligand E in toluene was heated to 100° C. with $Rh(CO)_2$acac and aqueous $H_3PO_4$ for 4 hours. A $^{31}$P-NMR spectrum of the yellow, homogeneous reaction mixture was subsequently measured. No traces of degradation products were found.

Example 26

Reaction of Ligand E with Air in the Presence of Catalysts

Ligand E together with $Rh(CO)_2$acac were dissolved in toluene and stirred overnight in air at room temperature. Examination by $^{31}$P-NMR showed that 100% of the ligand had been oxidized to the dioxide. $H_3PO_4$ was subsequently added and the mixture was again stirred overnight at room temperature. Examination by $^{31}$P-NMR showed that the dioxide was completely unchanged. From this experiment, it can be seen that although ligand E can, like all phosphorus ligands, be oxidized in the presence of metals and air, the oxides formed do not react further to give troublesome degradation products.

Example 27

Hydroformylation of a Butene/butane Mixture Using Ligand F

Ligand F displays a singlet at +105 ppm in the $^{31}$P-NMR ($C_6D_6$).

5.9 mg of $Rh(CO)_2$acac and 158 mg of ligand E (106 ppm of Rh, ligand:metal=10/1) were weighed out separately, each dissolved in 7.5 g of toluene, mixed and treated at 100° C. with 10 bar of synthesis gas ($CO:H_2$=1:2). After 60 minutes, the mixture was depressurized, 5.9 g of butene/butane mixture (45% of 1-butene, 40% of 2-butene, 15% of butanes) were then injected and the mixture was hydroformylated at 120° C. and 20 bar ($CO:H_2$=1:1) for 4 hours. The conversion of butenes was 87%, the aldehyde selectivity was 90% and the linearity was 94%.

Examination of the reaction product mixture by $^{31}$P-NMR showed no degradation products of the ligand. The reaction product mixture was a yellow homogeneous solution. A red precipitate was not observed. The experiment was repeated in the same autoclave and gave the same result.

Example 28

Continuous Hydroformylation of 1-octene Using Ligand E

In a continuously operated apparatus comprising an autoclave, pressure separator, wiped film evaporator (operated at 140° C.) and mixing vessel, 1-octene was hydroformylated by means of synthesis gas ($CO:H_2$=1:2) at 120° C. and a pressure of 20 bar (100 ppm of Rh, ligand:metal ratio=20:1). Averaged over a period of days, the follow result was obtained: conversion=61%, aldehyde selectivity=60%, linearity=84%. Over the entire period, neither additional rhodium nor additional ligand was added. After the end of the experiment, a homogeneous, light-yellow solution was present. Unspecific ligand decomposition could not be detected.

Example 29

Synthesis of Ligand G 15.6 g (118.9 mmol) of 3-methylindole (ligand G) were dissolved in 400 g of toluene at room temperature and cooled to −75° C. Firstly 56.9 g (563.4 mol) of triethylamine and then 8.14 g (59.4 mmol) of $PCl_3$ were subsequently added by means of a syringe. The mixture was slowly warmed to room temperature and subsequently refluxed for 16 hours. 13.7 g (38.8 mmol) of xanthenediol were then added at room temperature as a suspension in toluene and the mixture was refluxed overnight. The triethylamine hydrochloride formed was filtered off and washed once with toluene. After evaporation of the organic phases, the residue was taken up in dichloromethane and washed through a 4×20 cm Silica 60 column using 300 ml of dichloromethane. The ashing solution was evaporated and 100 ml of methanol were then added, forming a white sticky mass from which the solvent was separated by decantation. After stirring with pentane, the product was obtained as a fine white solid in a yield of 64%. ($^{31}$P-NMR: 105 ppm).

Example 30

Hydroformylation of a Butene/butane Mixture Using Ligand G 4.4 mg of $Rh(CO)_2acac$ and 156 mg of ligand G (98 ppm of Rh, ligand:metal=10/1) were weighed out separately, each dissolved in 6.4 g of toluene, mixed and treated at 100° C. with 10 bar of synthesis gas ($CO:H_2=1:2$). After 30 minutes, the mixture was depressurized, 4.9 g of butene/butane mixture (45% of 1-butene, 40% of 2-butene, 15% of butanes) were then injected and the mixture was hydroformylated at 110° C. and 15 bar ($CO:H_2=1:1$) for 4 hours. The conversion of butenes was 96%, the aldehyde selectivity was 100% and the linearity was 93%.

Example 31

Synthesis of Ligand H 35.6 g (242 mmol) of 5-methylindole were dissolved in 1 l of toluene at room temperature and cooled to −75° C. Firstly 123 g (1 222 mol) of triethylamine and then 16.5 g (120.4 mmol) of $PCl_3$ were subsequently added by means of a syringe. The mixture was slowly warmed to room temperature and subsequently stirred at 90–100° C. for 16 hours. 19 g (52.5 mmol) of xanthenediol were then added at room temperature as a suspension in toluene and the mixture was stirred overnight at 90–100° C. The triethylamine hydrochloride formed was filtered off and washed once with toluene. After evaporation of the organic phases, the residue was taken up in dichloromethane and washed through a 4×20 cm Silica 60 column using three 250 ml portions of dichloromethane. The washing solution was evaporated and 100 ml of methanol were then added, giving a white sticky mass from which the solvent was separated by decantation. After stirring with pentane, the product was obtained as a fine white solid in a yield of 64%. ($^{31}$P-NMR: 108 ppm).

Example 32

Hydroformylation of a Butene/butane Mixture Using Ligand H 3.0 mg of $Rh(CO)_2acac$ and 61 mg of ligand H (116 ppm of Rh, ligand:metal=5/1) were weighed out separately, each dissolved in 3.7 g of toluene, mixed and treated at 120° C. with 10 bar of synthesis gas ($CO:H_2=1:2$). After 30 minutes, the mixture was depressurized, 3.0 g of butene/butane mixture (45% of 1-butene, 40% of 2-butene, 15% of butanes) were then injected and the mixture was hydroformylated at 120° C. and 17 bar ($CO:H_2=1:1$) for 4 hours. The conversion of butenes was 98%, the aldehyde selectivity was 80% and the linearity was 93%.

Example 33

Synthesis of Ligand I a) Synthesis of Bisindolyl:

120 ml of THF were placed in a reaction vessel under nitrogen and 37 ml (425 mmol) of oxalyl chloride were added dropwise. After cooling to 0° C., a solution of 90 g (840 mmol) of o-toluidine and 117 ml (840 mmol) of triethylamine in 190 ml of THF was added dropwise over a period of 1 hour. The mixture was stirred at 0° C. for 2 hours, and then allowed to warm to room temperature while stirring. About 600 ml of water and then 900 ml of ethyl acetate were carefully added and the mixture was heated to 100° C. The solid formed was filtered off and washed with petroleum ether. Yield: 65%.

33.5 g (859 mmol) of potassium were added while stirring to 600 ml of tert-butanol and the mixture was stirred at 50° C. for 4 hours, until all of the potassium had reacted. 46 g (172 mmol) of N,N-bis-o-tolyloxamide were subsequently added. The mixture was heated on a sand bath, and the tert-butanol distilled off completely at 88° C. When the solvent had been removed, the temperature rose to 190° C. and a white voluminous solid sublimed off. The reaction temperature then rose to 300° C. and was maintained for 1 hour. The mixture was subsequently cooled to room temperature. 300 ml of water were carefully added. The solid was filtered off with suction and refluxed with 200 ml of ethanol. The solid was subsequently filtered off with suction, washed with pentane and dried. Yield: 50%.

b) Synthesis of Ligand I:

8.8 g (38 mmol) of bisindolyl together with 150 ml of THF were placed in a reaction vessel at −78° C. and admixed with 5.2 g (38 mmol) of $PCl_3$. 15 g (150 mmol) of triethylamine were subsequently added, and the mixture was warmed to room temperature overnight. 6.7 g of xanthenediol were suspended in 100 ml of THF and added to the reaction mixture, and the mixture was subsequently refluxed overnight. The triethylamine hydrochloride was filtered off, the solvent was removed from the filtrate under reduced pressure and the residue was stirred in dichloromethane. The solid formed was filtered off and dried. Yield: 40%. ($^{31}$P-NMR: 78 ppm).

Example 34

Hydroformylation of a Butene/butane Mixture Using Ligand I 5.1 mg of Rh(CO)$_2$acac and 175 mg of ligand I (101 ppm of Rh, ligand:metal=10/1) were weighed out separately, each dissolved in 9 g of THF, mixed and treated at 100° C. with 10 bar of synthesis gas (CO:H$_2$=1:2). After 30 minutes, the mixture was depressurized, 2.5 g of butene/butane mixture (45% of 1-butene, 40% of 2-butene, 15% of butanes) were then injected and the mixture was hydroformylated at 120° C. and 17 bar (CO:H$_2$=1:1) for 4 hours. The conversion of butenes was 40%, the aldehyde selectivity was 98% and the linearity was 68%.

Example 35

Synthesis of Ligand K 9 g (69 mmol) of ligand K were dissolved in xylene and admixed at −20° C. with 5.4 g (39 mmol) of PCl$_3$. 20 ml (145 mmol) of triethylamine were subsequently added slowly, the mixture was slowly warmed to room temperature and stirred overnight at 130° C. 6.6 g (17 mmol) of tetramethylxanthenediol were added at room temperature, and the mixture was stirred for 4 hours and then boiled overnight at 150° C. The triethylamine hydrochloride formed was filtered off, the xylene was removed under reduced pressure and the residue was dissolved in dichloromethane. The solution was purified over activated carbon and silica gel and the solvent was removed under reduced pressure. Yield: 37%. ($^{31}$P-NMR: 106 ppm).

Example 36

Hydroformylation of a Butene/butane Mixture Using Ligand K 5.1 mg of Rh(CO)$_2$acac and 166 mg of ligand K (101 ppm of Rh, ligand:metal=10/1) were weighed out separately, each dissolved in 7.5 g of toluene, mixed and treated at 100°0 C. with 10 bar of synthesis gas (CO:H$_2$=1:2). After 30 minutes, the mixture was depressurized, 5.0 g of butene/butane mixture (45% of 1-butene, 40% of 2-butene, 15% of butanes) were then injected and the mixture was hydroformylated at 120° C. and 17 bar (CO:H$_2$=1:1) for 4 hours. The conversion of butenes was 94%, the aldehyde selectivity was 98% and the linearity was 90%.

Example 37

Hydroformylation of a Butene/butane Mixture Using Ligand L

The synthesis of ligand L is carried out by a method analogous to that for the pyrrole derivative.

5.9 mg of Rh(CO)$_2$acac and 171 mg of ligand L (116 ppm of Rh, ligand:metal=10/1) were weighed out separately, each dissolved in 7.5 g of toluene, mixed and treated at 100° C. with 10 bar of synthesis gas (CO:H$_2$=1:2). After 30 minutes, the mixture was depressurized, 5.9 g of butene/butane mixture (45% of 1-butene, 40% of 2-butene, 15% of butanes) were then injected and the mixture was hydroformylated at 100° C. and 17 bar (CO:H$_2$=1:1) for 4 hours. The conversion of butenes was 16%, the aldehyde selectivity was 100% and the linearity was 94%.

What is claimed is:

1. A pnicogen chelate compound of the formula I

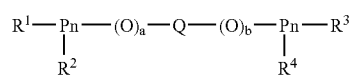

where
Q is a bridging group of the formula

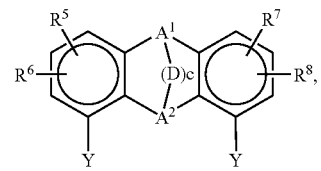

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl,
R$^d$ and R$^e$ are each, independently of one another, hydrogen, alkyl, cycloalkyl, heterocycloalkyl, aryl or hetaryl or the group R$^d$ together with a further group R$^d$ or the group R$^e$ together with a further group R$^e$ form an intramolecular bridging group D,
D is a divalent bridging group selected from among the, groups

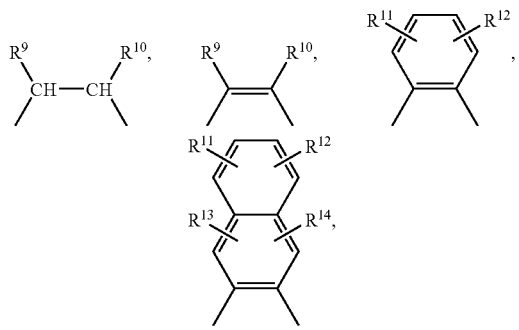

where
R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$–C$_4$-alkylene bridge,
R$^{11}$, R$^{12}$, R$^{13}$ and R$^{14}$ are each, independently of one another, hydrogen, alkyl, cycloalkyl, aryl, halogen, trifluoromethyl, COOH, carboxylate, cyano, alkoxy, SO$_3$H, sulfonate, NE$^1$E$^2$, alkylene-NE$^1$E$^2$E$^{3+}$X$^-$, acyl or nitro,
c is 0 or 1,
Y is a chemical bond,
R$^5$, R$^6$, R$^7$ and R$^8$ are each, independently of one another, hydrogen, alkyl, cycloalkyl, heterocycloalkyl, aryl, hetaryl, COOR$^f$, COO$^-$M$^+$, SO$_3$R$^f$, SO$_3^-$M$^+$, NE$^1$E$^2$, NE$^1$E$^2$E$^{3+}$X$^-$, alkylene-NE$^1$E$^2$E$^{3+}$X$^-$, OR$^f$, SR$^f$, (CHR$^g$CH$_2$O)$_x$R$^f$, (CH$^2$N(E$^1$))$_x$R$^f$, (CH$_2$CH$_2$N(E$^1$))$_x$R$^f$, halogen, trifluoromethyl, nitro, acyl or cyano, where R$^f$, E$^1$, E$^2$ and E$^3$ are identical or different radicals selected from among hydrogen, alkyl, cycloalkyl and aryl, R$^g$ is hydrogen, methyl or ethyl, M$^+$ is a cation, X$^-$ is an anion and x is an integer from 1 to b 120, or R$^5$ and/or R$^7$ together with two adjacent carbon atoms of the benzene ring to which they are bound form a fused ring system having 1, 2 or 3 further rings, a and b are each, independently of one another, b 0 or 1, Pn is a pnicogen atom selected from among the elements phosphorus, arsenic or antimony, and R$^1$, R$^2$, R$^3$, R$^4$ are each, independently of one another, hetaryl, hetaryloxy, alkyl, alkoxy, aryl, aryloxy, cycloalkyl, cycloalkoxy, heterocycloalkyl, heterocycloalkoxy or an NE$^1$E$^2$ group, with the proviso that R$^1$ and R$^3$ are pyrrole groups bound via the nitrogen atom to the pnicogen atom Pn, or R$^1$ together with R$^2$ and/or R$^3$ together with R$^4$ form a divalent group E of the formula Py—I—W containing at least one pyrrole group bound via the pyrrole nitrogen to the pnicogen atom Pn, where Py is a pyrrole group, I is a chemical bond or O, S, SiR$^a$R$^b$, NR$^c$ or CR$^h$R$^i$, W is cycloalkyl, cycloalkoxy, aryl, aryloxy, hetaryl or hetaryloxy, and R$^h$ and R$^i$ are each, independently of one another, hydrogen, alkyl, cycloalkyl, heterocycloalkyl, aryl or hetaryl, or form a bispyrrole group of the formula Py—I—Py bound via the nitrogen atoms to the pnicogen atom Pn.

2. A pnicogen chelate compound as claimed in claim 1 in which Pn is a phosphorus atom.

3. A pnicogen chelate compound as claimed in claim 1 in which R$^1$ and R$^3$ are unsubstituted pyrrolyl or imidazolyl groups bound via the pyrrole nitrogen to the pnicogen atom.

4. A pnicogen chelate compound as claimed in claim 1 in which R$^1$, R$^2$, R$^3$ and R$^4$ are unsubstituted pyrrolyl or imidazolyl groups bound via the pyrrole nitrogen to the pnicogen atom.

5. A pnicogen chelate compound as claimed in claim 1 in which R$^1$ and R$^3$ are each a pyrrole group bound via the pyrrole nitrogen to the pnicogen atom and selected from among the groups indolyl, pyrazolyl, indazolyl, benzotriazolyl, triazolyl, purinyl and carbazolyl.

6. A pnicogen chelate compound as claimed in claim 1 in which R$^1$ together with R$^2$ and/or R$^3$ together with R$^4$ form a substituted or unsubstituted bisindolediyl group of the formula

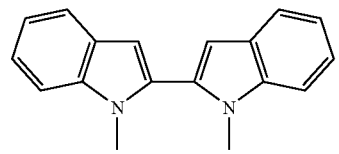

or a substituted or unsubstituted bispyrrolediylmethane group of the formula

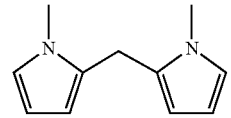

7. A pnicogen chelate compound as claimed in claim 1 in which the bridging group Q is a xanthenediyl group of the formula

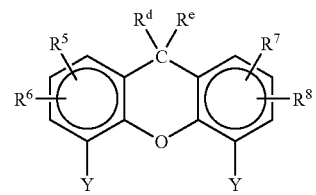

where R$^5$, R$^6$, R$^7$, R$^8$ and Y are as defined in claim 1 and R$^d$ and R$^e$ are each, independently of one another, hydrogen, alkyl, cycloalkyl, heterocyloalkyl, aryl or hetaryl.

8. A pnicogen chelate compound as claimed in claim 1 in which the bridging group Q is a triptycenediyl group of the formula

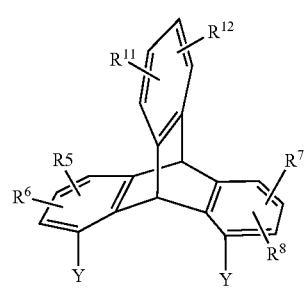

or the formula

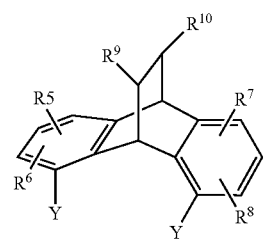

where $R^5$, $R^6$, $R^7$, $R^8$, $R^9$, $R^{10}$, $R^{11}$ and $R^{12}$ are as defined in claim 1.

9. A pnicogen chelate compound defined in claim 1 which is of the formula II

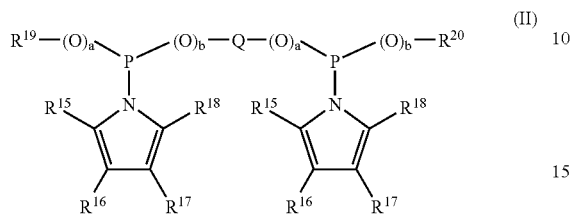
(II)

where
$R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^1$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$))$_y$R$^k$, (CH$_2$CH$_2$NE$^4$)$_y$R$^k$, halogen, trifluoromethyl, nitro, acyl or cyano, where
W' is a single bond, a heteroatom or a divalent bridging group having from 1 to 20 bridge atoms,
R$^k$, E$^4$, E$^5$, E$^6$ are identical or different radicals selected from among hydrogen, alkyl, cycloalkyl and aryl,
R$^1$ is hydrogen, methyl or ethyl,
M$^+$ is a cation equivalent,
X$^-$ is an anion equivalent and
y is an integer from 1 to 240,
where two adjacent radicals $R^{15}$, $R^{16}$, $R^{17}$ and $R^{18}$ together with the carbon atom of the pyrrole ring to which they, are bound may also form a fused ring system having 1, 2 or 3 further rings, with the proviso that at least one of the radicals $R^{15}$, $R^{16}$, $R^{17}$ and $R^{18}$ is not hydrogen and that $R^{19}$ and $R^{20}$ are not joined to one another,
$R^{19}$ and $R^{20}$ are each, independently of one another cycloalkyl, heterocycloalkyl, aryl or hetaryl,
a and b are each, independently of one another 0 or 1,
Pn is a pnicogen atom selected from among the elements phosphorus, arsenic or antimony, preferably phosphorus,
Q is a bridging group of the formula

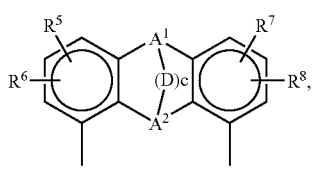

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl, R$^d$ and R$^e$ are each, independently of one another, hydrogen, alkyl, cycloalkyl, heterocycloalkyl, aryl or hetaryl or the group R$^d$ together with a further group R$^d$ or the group R$^e$ together with a further group R$^e$ form an intramolecular bridging group D,
D is a divalent bridging group selected from among the groups

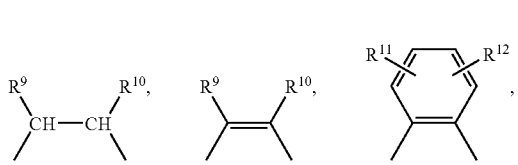

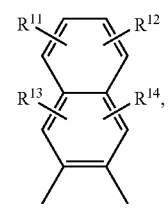

where
$R^9$ and $R^{10}$ are each, independently of one another, hydrogen, alkyl, cycloalkyl, aryl, halogen, trifluoromethyl, carboxyl, carboxylate or cyano or are joined to one another to form a C$_3$–C$_4$-alkylene bridge,
$R^{11}$, $R^{12}$, $R^{13}$ and $R^{14}$ are each, independently of one another, hydrogen, alkyl, cycloalkyl, aryl, halogen, trifluorumethyl, COOH, carboxylate, cyano, alkoxy, SO$_3$H, sulfonate, NE$^1$E$^2$, alkylene-NE$^1$E$^2$E$^{3+}$X$^-$, acyl or nitro,
c 0 is or 1,
$R^5$, $R^6$, $R^7$ and $R^8$ are each, independently of one another, hydrogen, alkyl, cycloalkyl, heterocycloalkyl, aryl, hetaryl, COOR$^f$, COO$^-$M$^+$, SO$_3$R$^f$, SO$_3$$^-$M$^+$, NE$^1$E$^2$, NE$^1$E$^2$E$^{3+}$X$^-$, alkylene-NE$^1$E$^2$E$^{3+}$X$^-$, OR$^f$, SR$^f$, (CHR$^g$CH$_2$O)$_x$R$^f$, (CH$_2$N(E$^1$))$_x$R$^f$, (CH$_2$CH$_2$N(E$^1$))$_x$R$^f$, halogen, trifluoromethyl, nitro, acyl or cyano,
where
R$^f$, E$^1$, E$^2$ and E$^3$ are identical or different radicals selected from among hydrogen, alkyl, cycloalkyl and aryl,
R$^g$ is hydrogen, methyl or ethyl,
M$^+$ is a cation,
X$^-$ is an anion and
x is an integer from 1 to 120,
or
$R^5$ and/or $R^7$ together with two adjacent carbon atoms of the benzene ring to which they are bound form a fused ring system having 1, 2 or 3 further rings.

10. A compound of the formula II as claimed in claim 9 which is selected from among compounds of the formulae II.1 to II.3

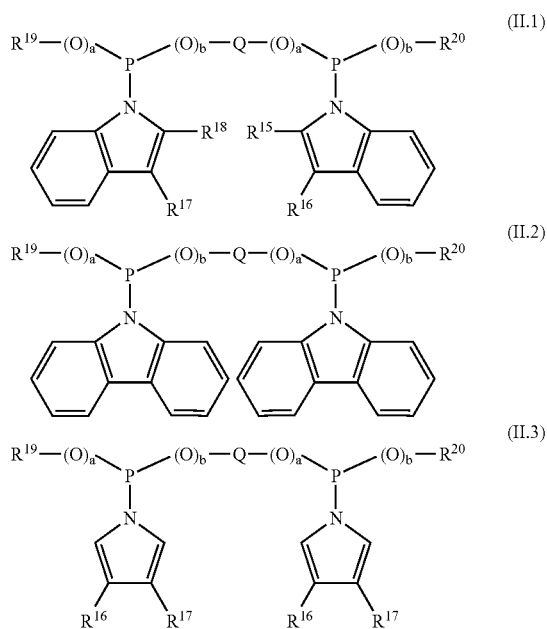

where $R^{15}$, $R^{16}$, $R^{17}$, $R^{18}$, Q, a and b are as defined in claim 9, where, in the formula II.3, at least one of the radicals $R^{16}$ and $R^{17}$ is not hydrogen, $R^{19}$ and $R^{20}$ are each, independently of one another, cycloalkyl, heterocycloalkyl, aryl or hetaryl.

11. A catalyst comprising a pnicogen chelate complex with a metal of transition group VIII of the Periodic Table of the Elements which comprises at least one pnicogen chelate compound as claimed in claim 1 as ligand.

12. A catalyst as claimed in claim 11 in which the metal is selected from among cobalt, rhodium, ruthenium and iridium.

13. A process or the hydroformylation of compounds containing at least one ethylenically unsaturated double bond by reaction with carbon monoxide and hydrogen in the presence of a catalyst as defined in claim 11.

14. A process for preparing aldehydes and/or alcohols by hydroformylation of $C_3$–$C_{20}$-olefins at superatmospheric pressure and elevated temperature by means of $CO/H_2$ mixtures in the, presence of a metal complex of a metal of transition group VIII of the Periodic Table of the Elements homogeneously dissolved in the reaction medium as catalyst and free ligand, wherein the catalyst comprises pnicogen chelate complex with a metal of transition group VII of the Periodic Table of Elements and a pnicogen chelate compound as claimed in claim 1, and the free ligand used is a pnicogen chelate compound as claimed in claim 1.

15. A process as claimed in claim 14, wherein a molar ratio of ligand to metal of transition group VIII of from 1:1 to 1000:1 is set in the reaction mixture.

16. A process for preparing 2-propylheptanol, which comprises a) hydroformylating butene or a butene-containing $C_4$-hydrocarbon mixture by means of carbon monoxide and hydrogen in the presence of a hydroformylation catalyst to give an n-valeraldehyde-containing hydroformylation product, where the hydroformylation catalyst comprises at least one complex of a metal of transition group VIII with at least one ligand of the formula I as defined in claim 1, b) optionally subjecting the hydroformylation product to a fractionation to give an n-valeraldehyde-enriched fraction, c) subjecting the hydroformylation product obtained in step a) or the n-valeraldehyde-enriched fraction obtained in step b) to an aldol condensation, d) catalytically hydrogenating the products of the aldol condensation by means of hydrogen to form alcohols, and e) optionally subjecting the hydrogenation products to a fractionation to give a 2propylheptanol-enriched fraction.

17. A process as claimed in claim 16, wherein the ligand of the formula I is selected from among compounds of the formula II

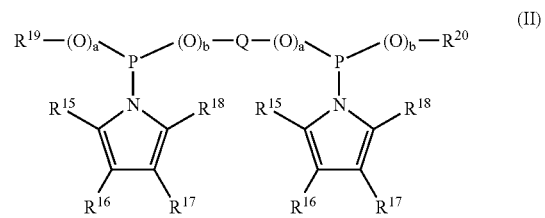

where $R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^l$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, where W' is a single bond, a heteroatom or a divalent bridging group having from 1 to 20 bridge atoms, $R^k$, $E^4$, $E^5$, $E^6$ are identical or different radicals selected from among hydrogen, alkyl, cycloalkyl and aryl, $R^1$ is hydrogen, methyl or ethyl, M$^+$ is a cation equivalent, X$^-$ is an anion equivalent and y is an integer from 1 to 240, where two adjacent radicals $R^{15}$, $R^{16}$, $R^{17}$ and $R^{18}$ together with the carbon atom of the pyrrole ring to which they, are bound may also form a fused ring system having 1, 2 or 3 further rings, with the proviso that at least one of the radicals $R^{15}$, $R^{16}$, $R^{17}$ and $R^{18}$ is not hydrogen and that $R^{19}$ and $R^{20}$ are not joined to one another, $R^{19}$ and $R^{20}$ are each, independently of one another cycloalkyl, heterocycloalkyl, aryl or hetaryl, a and b are each, independently of one another 0 or 1, Pn is a pnicogen atom selected from among the elements phosphorus, arsenic or antimony, preferably phosphorus, Q is a bridging group of the formula

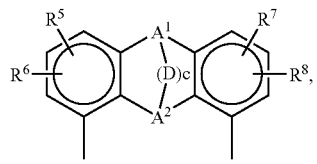

where

A¹ and A² are each, independently of one another, O, S, SiR$^a$R$^b$, NR$^c$ or CR$^d$R$^e$, where R$^a$, R$^b$ and R$^c$ are each, independently of one another, hydrogen, alkyl, cycloalkyl, heterocycloalkyl, aryl or hetaryl, R$^d$ and R$^e$ are each, independently of one another, hydrogen, alkyl, cycloalkyl, heterocycloalkyl, aryl or hetaryl or the group R$^d$ together with a further group R$^d$ or the group R$^e$ together with a further group R$^e$ form an intramolecular bridging group D, D is a divalent bridging group selected from among the groups

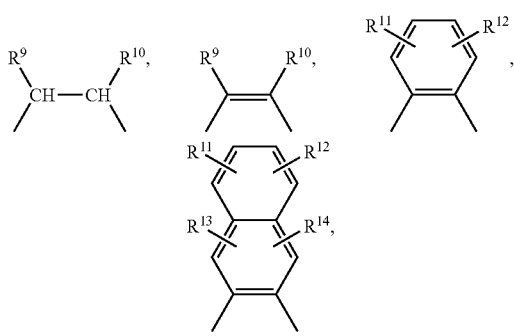

where

R⁹ and R¹⁰ are each, independently of one another, hydrogen, alkyl, cycloalkyl, aryl, halogen, trifluoromethyl, carboxyl, carboxylate or cyano or are joined to one another to form a $C_3$–$C_4$-alkylene bridge, R¹¹, R¹², R¹³ and R¹⁴ are each, independently of one another, hydrogen, alkyl, cycloalkyl, aryl, halogen, trifluorumethyl, COOH, carboxylate, cyano, alkoxy, SO³H, sulfonate, NE¹E², alkylene-NE¹ E²E³⁺X⁻, acyl or nitro, c 0 is or 1, R⁵, R⁶, R⁷ and R⁸ are each, independently of one another, hydrogen, alkyl, cycloalkyl, heterocycloalkyl, aryl, hetaryl, COOR$^f$, COO⁻M⁺, SO₃R$^f$, SO₃⁻M⁺, NE¹E², NE¹E²E³⁺X⁻, alkylene-NE¹E²E³⁺X⁻, OR$^f$, SR$^f$, (CHR$^g$CH₂O)$_x$R$^f$, (CH₂N(E¹))$_x$R$^f$, (CH₂CH₂N(E¹))$_x$R$^f$, halogen, trifluoromethyl, nitro, acyl or cyano, where R$^f$, E¹, E² and E³ are identical or different radicals selected from among hydrogen, alkyl, cycloalkyl and aryl, R$^g$ is hydrogen, methyl or ethyl, M⁺ is a cation, X⁻ is an anion and x is an integer from 1 to 120, or R⁵ and/or R⁷ together with two adjacent carbon atoms of the benzene ring to which they are bound form a fused ring system having 1, 2 or 3 further rings.

18. A catalyst comprising at least one compound of the formula I for hydroformylation, carbonylation, hydrocyanation or hydrogenation.

19. The catalyst for hydroformylation, carbonylation, hydrocyanation or hydrogenation defined in claim 18, wherein the compound of the formula I is a pnicogen chelate compound of the formula II

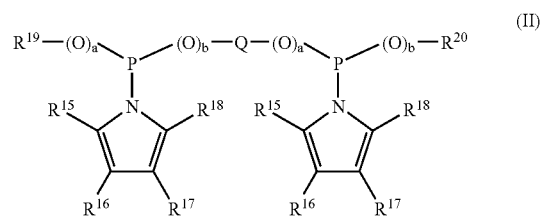

where

R¹⁵, R¹⁶, R¹⁷ and R¹⁸ are each, independently of one another, hydrogen, alkyl, cycloalkyl, heterocycloalkyl, aryl, hetaryl, W'COOR$^k$, W'COO⁻M⁺, W'(SO₃)R$^k$, W'(SO₃)⁻M⁺, W'PO₃(R$^k$)(R$^l$), W'(PO₃)²⁻(M⁺)₂, W'NE⁴E⁵, W'(NE⁴E⁵E⁶)⁺X⁻, W'OR$^k$, W'SR$^k$, (CHR¹CH₂O)$_y$R$^k$, (CH₂NE⁴)$_y$R$^k$, (CH₂CH₂NE⁴)$_y$R$^k$, halogen, trifluoromethyl, nitro, acyl or cyano, where W' is a single bond, a heteroatom or a divalent bridging group having from 1 to 20 bridge atoms, R$^k$, E⁴, E⁵, E⁶ are identical or different radicals selected from among hydrogen, alkyl, cycloalkyl and aryl, R¹ is hydrogen, methyl or ethyl, M⁺ is a cation equivalent, X⁻ is an anion equivalent and y is an integer from 1 to 240, where two adjacent radicals R¹⁵, R¹⁶, R¹⁷ and R¹⁸ together with the carbon atom of the pyrrole ring to which they are bound may also form a fused ring system having 1, 2 or 3 further rings, with the proviso that at least one of the radicals R¹⁵, R¹⁶, R¹⁷ and R¹⁸ is not hydrogen and that R¹⁹ and R²⁰ are not joined to one another, R¹⁹ and R²⁰ are each, independently of one another cycloalkyl, heterocycloalkyl, aryl, or hetaryl, a and b are each, independently of one another 0 or 1, Pn is a pnicogen atom selected from among the elements phosphorus, arsenic or antimony, preferably phosphorus, Q is a bridging group of the formula

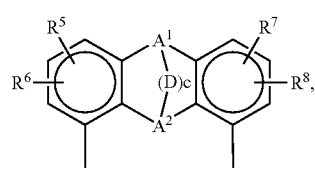

where

A¹ and A² are each, independently of one another, O, S, SiR$^a$R$^b$, NR$^c$ or CR$^d$R$^e$, where $R^a$, $R^b$ and $R^c$ are each, independently of one another, hydrogen, alkyl, cycloalkyl, heterocycloalkyl, aryl or hetaryl, $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ form an intramolecular bridging group D, D is a divalent bridging group selected from among the groups

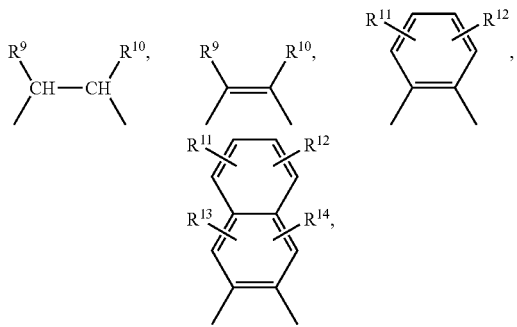

where $R^9$ and $R^{10}$ are each, independently of one another, hydrogen, alkyl, cycloalkyl, aryl, halogen, trifluoromethyl, carboxyl, carboxylate or cyano or are joined to one another to form a $C_3$–$C_4$-alkylene bridge, $R^{11}$, $R^{12}$, $R^{13}$ and $R^{14}$ are each, independently of one another, hydrogen, alkyl, cycloalkyl, aryl, halogen, trifluorumethyl, COOH, carboxylate, cyano, alkoxy, $SO^3H$, sulfonate, $NE^1E^2$, alkylene-$NE^1 E^2E^{3+}X^-$, acyl or nitro, c 0 is or 1, $R^5$, $R^6$, $R^7$ and $R^8$ are each, independently of one another, hydrogen, alkyl, cycloalkyl, heterocycloalkyl, aryl, hetaryl, $COOR^f$, $COO^-M^+$, $SO_3R^f$, $SO_3^-M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano, where $R^f$, $E^1$, $E^2$ and $E^3$ are identical or different radicals selected from among hydrogen, alkyl, cycloalkyl and aryl, $R^g$ is hydrogen, methyl or ethyl, $M^+$ is a cation, $X^-$ is an anion and x is an integer from 1 to 120, or $R^5$ and/or $R^7$ together with two adjacent carbon atoms of the benzene ring to which they are bound form a fused ring system having 1, 2 or 3 further rings.

20. The pnicogen chelate compound of the formula I defined in claim 1, wherein the pyrrole groups in the position of $R^1$ and $R^3$ and the pyrrole group represented by Py is an unsubstituted or substituted heteroaromatic group which contains a pyrrolic nitrogen atom which can be covalently bound.

21. The pnicogen chelate compound of the formula I defined in claim 1, wherein the pyrrole groups in the position of $R^1$ and $R^3$ and the pyrrol group represented by Py are selected from the group of unsubstituted and substituted pyrrolyl, imidazolyl, pyrazolyl, indolyl, purinyl, indazolyl, benzotriazolyl, 1,2,3-triazolyl, 1,3,4-triazolyl and carbazolyl rings.

* * * * *